United States Patent
Leon et al.

(10) Patent No.: US 11,655,294 B2
(45) Date of Patent: May 23, 2023

(54) METHODS AND COMPOSITIONS FOR THE TREATMENT OF CELIAC DISEASE, NON-CELIAC GLUTEN SENSITIVITY, AND REFRACTORY CELIAC DISEASE

(71) Applicants: Celimmune LLC, Thousand Oaks, CA (US); AMGEN INC., Thousand Oaks, CA (US)

(72) Inventors: Francisco Leon, Bethesda, MD (US); Wayne H. Tsuji, Seattle, WA (US)

(73) Assignees: AMGEN INC., Thousand Oaks, CA (US); CELIMMUNE LLC, Thousand Oaks, CA (US)

( * ) Notice: Subject to any disclaimer, the term of this patent is extended or adjusted under 35 U.S.C. 154(b) by 0 days.

(21) Appl. No.: 16/741,897

(22) Filed: Jan. 14, 2020

(65) Prior Publication Data

US 2020/0385451 A1  Dec. 10, 2020

Related U.S. Application Data

(63) Continuation of application No. 15/622,990, filed on Jun. 14, 2017, now abandoned.

(60) Provisional application No. 62/350,660, filed on Jun. 15, 2016.

(51) Int. Cl.
| | | |
|---|---|---|
| *C07K 16/24* | (2006.01) | |
| *A61K 39/395* | (2006.01) | |
| *A61K 39/00* | (2006.01) | |

(52) U.S. Cl.
CPC .......... *C07K 16/243* (2013.01); *A61K 39/395* (2013.01); *C07K 16/244* (2013.01); *A61K 2039/505* (2013.01); *A61K 2039/54* (2013.01); *A61K 2039/545* (2013.01); *C07K 2317/21* (2013.01); *C07K 2317/56* (2013.01)

(58) Field of Classification Search
None
See application file for complete search history.

(56) References Cited

U.S. PATENT DOCUMENTS

| | | |
|---|---|---|
| 4,439,196 A | 3/1984 | Higuchi |
| 4,447,224 A | 5/1984 | Decant, Jr. et al. |
| 4,447,233 A | 5/1984 | Mayfield |
| 4,475,196 A | 10/1984 | La Zor |
| 4,486,194 A | 12/1984 | Ferrara |
| 4,487,603 A | 12/1984 | Harris |
| 4,522,811 A | 6/1985 | Eppstein et al. |
| 4,596,556 A | 6/1986 | Morrow et al. |
| 4,790,824 A | 12/1988 | Morrow et al. |
| 4,941,880 A | 7/1990 | Burns |
| 5,064,413 A | 11/1991 | McKinnon et al. |
| 5,312,335 A | 5/1994 | McKinnon et al. |
| 5,374,548 A | 12/1994 | Caras |
| 5,383,851 A | 1/1995 | McKinnon, Jr. et al. |
| 5,399,163 A | 3/1995 | Peterson et al. |
| 5,399,331 A | 3/1995 | Loughrey et al. |
| 5,416,016 A | 5/1995 | Low |
| 7,153,507 B2 | 12/2006 | Van De Winkel et al. |
| 7,247,304 B2 | 7/2007 | Van De Winkel et al. |
| 7,329,405 B2 | 2/2008 | Van De Winkel et al. |
| 7,585,961 B2 | 9/2009 | Van De Winkel et al. |
| 7,597,892 B2 | 10/2009 | Van De Winkel et al. |
| 8,345,105 B2 | 1/2013 | Fisher et al. |

FOREIGN PATENT DOCUMENTS

| | | | |
|---|---|---|---|
| WO | WO000002582 | * | 1/2000 |
| WO | 2004/076620 A2 | | 9/2004 |
| WO | 2007/087384 A2 | | 8/2007 |
| WO | 2016/001275 A1 | | 1/2016 |

OTHER PUBLICATIONS

Leon et al, (Drug Discovery World; Mar. 2015; vol. 16, No. 2, pp. 73-78).*
Vicari, MABS, 2017, vol. 9, No. 6, pp. 927-944.*
Kulkarni et al, (European Journal of Pharmacology 909 (2021) 174434, p. 1-8.*
Berge et al., "Pharmaceutical Salts," *Journal of Pharmaceutical Sciences* 66(1):1-19 (1977).
Bird et al., "Single-Chain Antigen-Binding Proteins," *Science* 242:423-426 (1988).
Blaser et al., "Donor-derived IL-15 is critical for acute allogeneic graft-versus-host-disease," *Blood* 105(2):894-901 (2005).
Bloeman et al., "Adhesion molecules: a new target for immunoliposome-mediated drug delivery," *FEBS Letters* 357:140-144 (1995).
Brar et al., "Budesonide in the Treatment of Refractory Celiac Disease," *American Journal of Gastroenterology* 102:2265-2269 (2007).
Catassi et al., "A prospective, double-blind, placebo-controlled trial to establish a safe gluten threshold for patients with celiac disease," *Am J Clin Nutr* 85(1):160-166 (2007).
Conti et al., "Interleukin-15 Production During Liver Allograft Rejection in Humans," *Transplantation* 76(1):210-216 (2003).
Cranney et al., "The Canadian Celiac Health Survey," *Dig Dis Sci.* 52(4):1087-1095 (2007).
Cunningham-Rundles et al., "Biological activities of polyethylene-glycol immunoglobulin conjugates," *Journal of Immunological Methods* 152:177-190 (1992).
DePaolo et al., "Co-Adjuvant effects of retinoic acid and IL-15 induce inflammatory immunity to dietary antigens," *Nature* 471:220-224 (2011).
Di Sabatino et al., "Small Amounts of Glutenin Subjects With Suspected Nonceliac Gluten Sensitivity: A Randomized, Double-Blind, Placebo-Controlled, Cross-Over Trial" *Clinical Gastroenterology and Hepatology* 13:1604-1612 (2015).

(Continued)

*Primary Examiner* — Bridget E Bunner
*Assistant Examiner* — Fozia M Hamud
(74) *Attorney, Agent, or Firm* — Amy C. Madl

(57) ABSTRACT

Methods and pharmaceutical compositions are provided herein for the treatment of inflammatory disorders, in particular celiac disease, refractory celiac disease and non-celiac gluten sensitivity.

7 Claims, 18 Drawing Sheets

Specification includes a Sequence Listing.

(56) References Cited

OTHER PUBLICATIONS

Di Sabatino et al., "Role of IL-15 in immune-mediated and infectious diseases," *Cytokine & Growth Factor Reviews* 22:19-33 (2011).
Donnelly et al., "Pharmacotherapy and management strategies for coeliac disease," *Expert Opinion on Pharmacotherapy* 12(11):1731-1744 (2011).
Elli et al., "Evidence for the Presence of Non-Celiac Gluten Sensitivity in Patients with Functional Gastrointestinal Symptoms : Results from a Multi center Randomized Double-Blind Placebo-Controlled Gluten Challenge," *Nutrients* 8(2):84, doi:10.3390/nu8020084 (2016).
Fehniger et al., "Interleukin 15: biology and relevance to human disease," *Blood* 97(1):14-32 (2001).
Gianfrani et al., "Adaptive and innate immune responses in celiac disease," *Immunology Letters* 99(2):141-145 (2005).
Gibert et al., "Consumption of gluten-free products: should the threshold value for trace amounts of gluten be at 20, 100 or 200 p.p.m.?" *European Journal of Gastroenterology & Hepatology* 18:1187-1195 (2006).
Goerres et al., "Azathioprine and prednisone combination therapy in refractory coeliac disease," *Aliment Pharmacol Ther* 18:487-494 (2003).
Gorski et al., "The Fully Human Anti-IL-15 Antibody AMG 714, in Development for Celiac and Refractory Celiac Disease, Does Not Reduce Circulating Numbers of Human Natural Killer Cells or Preclude Their In Vitro Activation and Fuction," abstract, *Gastroenterology*, (2016).
Green et al., "Celiac Disease," *The New England Journal of Medicine* 357(17):1731-1743 (2007).
Hopper et al., "Pre-endoscopy serological testing for coeliac disease: evaluation of a clinical decision tool," *Br Med Journal* 334(7596):729 (2007).
Huston et al., "Protein engineering of antibody binding site: Recovery of specific activity in an anti-digoxin single-chain Fv analogue produced in *Escherichia coli*," *Proc. Natl. Acad. Sci. USA* 85:5879-5883 (1988).
Keinanen and Laukkanen, "Biosynthetic lipid-tagging of antibodies," *FEBS Letters* 346:123-126 (1994).
Kennedy et al., "Reversible Defects in Natural Killer and Memory CD8 T Cell Lineages in Interleukin 15-deficient Mice," *J Exp Med.* 191(5):771-780 (2000).
Killion and Fidler, "Systemic Targeting of Liposome-Encapsulated Immunomodulators to Macrophages for Treatment of Cancer Metastasis," *Immunomethods* 4:273-279 (1994).
Korneychuk et al., "Interleukin 15 and CD4+ T Cells Cooperate to Promote Small Intestinal Enteropathy in Response to Dietary Antigen," *Gastroenterology* 146:1017-1027 (2014).
Landor, "Maternal-fetal transfer of immunoglobulins," *Ann Allergy Asthma Immunol* 74:279-283 (1995).
Lebrec et al., "Homeostasis of Human NK Cells Is Not IL-15 Dependent," *J Immunol.* 191(11):5551-5558 (2013).
Lebwohl et al., "Mucosal Healing and Risk for Lymphoproliferative Malignancy in Celiac Disease," *Ann Intern Med.* 159(3):169-175 (2013).
Lee et al., "Duodenal histology in patients with celiac disease after treatment with a gluten-free diet," *Gastrointestinal Endoscopy* 57(2):187-191 (2003).
Litinskiy et al., "DCs induce CD40-independent immunoglobulin class switching through BLyS and APRIL," *Nat Immunol.* 3(9):822-829 (2002).
Lodolce et al., "IL-15 Receptor Maintains Lymphoid Homeostasis by Supporting Lymphocyte Homing and Proliferation," *Immunity* 9(5):669-676 (1998).
Lundin and Alaedini, "Non-celiac Gluten Sensitivity," *Gastrointestinal Endoscopy Clinics of North America* 22:723-734 (2012).
Malamut et al., "IL-15 triggers an antiapoptotic pathway in human intraepithelial lumphocytes that is a potential new target in celiac disease—associated inflammation and lymphomagenesis," *The Journal of Clinical Investigation* 120(6):2131-2143 (2010).
McCarville et al., "Pharmacological approaches in celiac disease," *Current Opinion in Pharmacology* 25:7-12 (2015).
McInnes and Gracie, "Interleukin-15: a new cytokine target for the treatment of inflammatory diseases," *Curr Opin Pharmacol* 4(4):392-397 (2004).
Meresse et al, "Celiac Disease: An Immunological Jigsaw," *N. Immunity.* 36:907-919 (2012).
Midhagen and Hallert, "High Rate of Gastrointestinal Symptoms in Celiac Patients Living on a Gluten-Free Diet: Controlled Study," *Am J Gastroenterol.* 98(9):2023-2026 (2003).
Needleman and Wunsch, "A General Method Applicable to the Search for Similarities in the Amino Acid Sequence of Two Proteins," *J Mol. Biol.* (48):443-453 (1970).
Nijeboer et al. "Therapy in RCDII: Rationale for Combination Strategies?" *Dig Dis.* 33:227-230 (2015).
Owais et al., "Chloroquine Encapsulated in Malaria-Infected Erythrocyte-Specific Antibody-Bearing Liposomes Effectively Controls Chloroquine-Resistant *Plasmodium berghei* Infections in Mice," *Antimicrob. Agents Chemother.* 39(1):180-184 (1995).
Park et al., "Follicular Dendritic Cells Produce IL-15 That Enhances Germinal Center B Cell Proliferation in Memebrane-Bound Form," *J Immunol.* 173(11):6676-6683 (2004).
Ranade, "Drug Delivery Systems. 1. Site-Specific Drug Delivery Using Liposomes as Carriers," *J Clin. Pharmacol.* 29:685-694 (1989).
Rubio-Tapia et al., "ACG Clinical Guidelines: Diagnosis and Management of Celiac Disease," *Am J Gastroenterol.* 108:656-676 (2013).
Schluns et al., "The roles of interleukin-15 receptor α: Trans-presentation, receptor component, or both?" *Int J Biochem Cell Biol.* 37(8):1567-1571 (2005).
Schreier et al., "Targeting of Liposomes to Cells Expressing CD4 Using Glycosylphosphatidylinositol-anchored gp120," *J. Biol. Chem.* 269(12):9090-9098 (1994).
Shah et al., "Patient Perception of Treatment Burden Is High in Celiac Disease Compared With Other Common Conditions," *Am J Gastroenterol.* 109(9):1304-1311 (2014).
Sharaiha et al., "Increasing Incidence of Enteropathy-Associated T-Cell Lymphoma in the United States," *Cancer* 118:3786-3792 (2012).
Stein and Schuppan, "Coeliac Disease—New Pathophsiological Findings and Their Implications for Therapy," *Viszeralmedizin* 30(3):156-165 (2014).
Strejan et al., "Suppression of Chronic-Relapsing Experimental Allergic Encephalomyelitis in Strain-13 Guinea Pigs by Administration of Liposome-Associated Myelin Basic Protein," *J. Neuroimmunol.* 7:27-41 (1984).
Taavela et al., "Degree of Damage to the Small Bowel and Serum Antibody Titers Correlate With Clinical Presentation of Patients With Celiac Disease," *Clinical Gastroenterology and Hepatology* 11: 166-171 (2013).
Tack et al., "Evaluation of Cladribine treatment in refractory celiac disease type II," *World J Gastroenterol* 17(4):506-513 (2011).
Tack et al., "Auto-SCT in refractory celiac disease type II patients unresponsive to cladribine therapy," *Bone Marrow Transplantation* 46:840-846 (2011).
Umezawa and Eto, "Liposome Targeting to Mouse Brain: Mannose as a Recognition Marker," *Biochem. Biophys. Res. Commun.* 153(3):1038-1044 (1988).
Van Wanrooij et al., "Optimal Strategies to Identify Aberrant Intra-Epithelial Lymphocytes in Refractory Coeliac Disease," *J Clin Immunol* 34:828-835 (2014).
Verbeek et al., "Novel approaches in the management of refractory celiac disease," *Expert Rev Clin Immunol* 4(2):205-219 (2008).
Ward et al., "Binding activities of a repertoire of single immunoglobulin variable domains secreted from *Escherichia coli*," *Nature* 341:544-546 (1989).
Yokoyama et al., "Antibody-mediated blockade of IL-15 reverses the autoimmune intestinal damage in transgenic mice that overexpress IL-15 in enterocytes," *Proc Natl Acad Sci USA* 106(37): 15849-15854 (2009).

(56) References Cited

OTHER PUBLICATIONS

Yokoyama et al., "Transgenic Mice that Overexpress Human IL-15 in Enterocytes Recapitulate Both B and T Cell-Mediated Pathologic Manifestations of Celiac Disease," *J Clin Immunol.* 31(6):1038-1044 (2011).
Anonymous, "A Double-Blind, Placebo Controlled, Randomized, Parallel-Group Clinical Trial With Multiple Dose Treatment of Anti-IL 15 Human Monoclonal Antibody (AMG 714) in Patients With Active Rheumatoid Arthritis Who Have Previously Failed One or More Disease Modifying Anti-Rheumatic Drugs," ClinicalTrials.gov, Identifier: NCT00433875 (2016).
Anonymous, "A Phase 2a, Randomized, Double-Blind, Placebo-Controlled, Parallel-Group Study to Evaluate the Efficacy and Safety of AMG 714 in Adult Patients With Type II Refractory Celiac Disease, an In Situ Small Bowel T Cell Lymphoma," History of Changes for Study: NCT02633020 dated Dec. 17, 2015, ClinicalTrials.gov, Identifier: NCT02633020.
Anonymous, "A Phase 2a, Randomized, Double-Blind, Placebo-Controlled, Parallel-Group Study to Evaluate the Efficacy and Safety of AMG 714 in Adult Patients With Type II Refractory Celiac Disease, an In Situ Small Bowel T Cell Lymphoma," History of Changes for Study: NCT02633020 dated Dec. 22, 2015, ClinicalTrials.gov, Identifier: NCT02633020.
Anonymous, "A Phase 2a, Randomized, Double-Blind, Placebo-Controlled, Parallel-Group Study to Evaluate the Efficacy and Safety of AMG 714 in Adult Patients With Type II Refractory Celiac Disease, an In Situ Small Bowel T Cell Lymphoma," History of Changes for Study: NCT02633020 dated Apr. 20, 2016, ClinicalTrials.gov, Identifier: NCT02633020.
Anonymous, "A Phase 2a, Randomized, Double-Blind, Placebo-Controlled, Parallel-Group Study to Evaluate the Efficacy and Safety of AMG 714 in Adult Patients with Celiac Disease," History of Changes for Study: NCT02637141 dated Dec. 22, 2015 ClinicalTrials.gov, Identifier: NCT02637141.
Anonymous, "A Phase 2a, Randomized, Double-Blind, Placebo-Controlled, Parallel-Group Study to Evaluate the Efficacy and Safety of AMG 714 in Adult Patients with Celiac Disease," History of Changes for Study: NCT02637141 dated Apr. 20, 2016 ClinicalTrials.gov, Identifier: NCT02637141.
Atzeni and Sarzi-Puttini, "Anti-cytokine antibodies for rheumatic diseases," *Current Opinion in Investigational Drugs* 10(11): 1204-1211 (2009).
Escudero-Hernandez et al., "Association of the IL-15 and IL-15Rα genes with celiac disease," *Cytokine* 99: 73-79 (2017).
Ettersperger et al., "Interleukin-15-Dependent T-Cell-like Innate Intraepithelial Lymphocytes Develop in the Intestine and Transform into Lymphomas in Celiac Disease," *Immunity* 45: 610-625 (2016).
Gabay and McInnes, "The biological and clinical importance of the 'new generation' cytokines in rheumatic diseases," *Arthritis Research & Therapy* 11: 1-14 (2009).
Leffler et al., "Development of Celiac Disease Therapeutics: Report of the Third Gastroenterology Regulatory Endpoints and Advancement of Therapeutics Workshop," *Gastroenterology* 151:407-411 (2016).
Schmitz et al., "Identification of a potential physiological precursor of aberrant cells in refractory coeliac disease type II," *Gut* 62: 509-519 (2013).
Vaquero et al., "Challenges to drug discovery for celiac disease and approaches to overcome them," *Expert Opinion on Drug Discovery* 14(10):957-968 (2019).
Sollid and Khosla, "Novel therapies for coeliac disease," *Journal of Internal Medicine* 269(6): 604-613 (2011).
Sollid and Lundin, "Diagnosis and treatment of celiac disease," *Mucosal Immunology* 2(1): 3-7 (2009).
Anonymous, "Phase 2 study of AMG 714 for refractory celiac disease begins enrollment," (2016).
Anonymous, "Celimmune Commences First-Ever Dosing with AMG 714 in Celiac Disease," Celimmune, Retrieved: http//celimmune.com/celimmune-dosing-amg-714-in-phase-2-celiac-disease-study/.
Anonymous, "A Randomized, Double-blind, Placebo-controlled, Ascending Dose Study to Evaluate the Safety, Pharmacokinetics, and Efficacy of AMG 714 After Multiple Dose Administration in Subjects With Moderate to Severe Psoriasis," ClinicalTrials.gov, Identifier: NCT00443326, (2016).
Anonymous, "A Phase 2a, Randomized, Double-Blind, Placebo-Controlled, Parallel-Group Study to Evaluate the Efficacy and Safety of AMG 714 in Adult Patients With Type II Refractory Celiac Disease, an In Situ Small Bowel T Cell Lymphoma," ClinicalTrials.gov, Identifier: NCT02633020, (2016).
Anonymous, "A Phase 2a, Randomized, Double-Blind, Placebo-Controlled, Parallel-Group Study to Evaluate the Efficacy and Safety of AMG 714 in Adult Patients with Celiac Disease," ClinicalTrials.gov, Identifier: NCT02637141 (2016).
Abadie V. et al., "IL-15: a central regulator of celiac disease immunopathology," *Immunological Reviews* 260:221-234 (2014).
Altschul, et al., "Basic Local Alignment Search Tool," *J. Mol. Biol.* 215:403-10 (1990).
Anthony et al., "Soluble Interleukin-15 Complexes Are Generated In Vivo by Type I Interferon Dependent and Independent Pathways," *PLoS One* 10(3):e0120274, Mar. 2015.
Baslund et al., "Targeting Interleukin-15 in Patients With Rheumatoid Arthritis," *Arthritis & Rheumatism* 52(9):2686-2692 (2005).

* cited by examiner

METHODS AND COMPOSITIONS FOR THE TREATMENT OF CELIAC DISEASE, NON-CELIAC GLUTEN SENSITIVITY, AND REFRACTORY CELIAC DISEASE

CROSS REFERENCE TO RELATED APPLICATIONS

This application is a continuation application of U.S. patent application Ser. No. 15/622,990, filed Jun. 14, 2017, which claims priority to and the benefit of U.S. Provisional Application No. 62/350,660 filed Jun. 15, 2016, all of which are incorporated by reference herein in their entireties.

FIELD

The compositions and methods disclosed herein relate to the treatment of inflammatory disorders, in particular Celiac Disease, Refractory Celiac Disease and Non-celiac gluten sensitivity.

REFERENCE TO THE SEQUENCE LISTING

This application contains a Sequence Listing in computer-readable form. The Sequence Listing is provided as a text file entitled A-2082-US-CNT_SeqList_ST25.txt, created Jan. 10, 2020, which is 4,703 bytes in size. The information in the electronic format of the Sequence Listing is incorporated herein by reference in its entirety.

BACKGROUND

Celiac disease (CD) is a systemic autoimmune disease triggered by gluten consumption in genetically susceptible individuals (Green and Cellier, 2007). CD results in debilitating symptoms, including gut mucosal damage and potentially serious medical complications.

CD was the first autoimmune disease with an identified antigen, gluten, the main protein present in some of the most common cereals (e.g., wheat, barley, rye). Humans lack enzymes to fully digest gluten, which, in the right genetic context, triggers inflammation and autoimmunity in the gut and other organs following deamination by the enzyme transglutaminase (tTG). CD presents in a several forms, presenting challenges for treatment.

CD is the only common autoimmune disorder with no approved medication. Currently, the only available strategy for the management of CD is a lifelong total avoidance of gluten. The ubiquitous presence of gluten makes total avoidance very difficult, if not impossible. As little as 50 mg/day (a normal diet contains greater than 10 g/day) triggers activation of T cells in the small bowel and causes intestinal mucosal damage (Catassi et al., 2007). For this reason, more than 50% of CD patients on a gluten free diet (GFD) continue to present with active disease and intestinal immune activation and mucosal atrophy (Lee et al., 2003; Cranney et al., 2007; Hopper et al., 2007; Midhagen et al., 2003). Approximately 20% of individuals diagnosed with celiac disease have persistent symptoms or anemia with or without a positive tissue transglutaminase antibody (a molecular marker indicating celiac).

Non-Responsive Celiac Disease (NRCD) is defined by the persistent signs, symptoms or laboratory abnormalities typical of CD, despite abstaining from dietary gluten for six to twelve months (Rubio-Tapia et al., 2013). Currently there are no effective treatments for NRCD.

Refractory Celiac Disease (RCD) is characterized by a rare but specific complication of persistent exposure to gluten in CD, which affects approximately 1% of celiac patients (Lebwohl et al., 2013). RCD is characterized by severe intestinal mucosal atrophy and gastrointestinal symptoms in the absence of gluten consumption and in the presence of small bowel aberrant intestinal intra-epithelial lymphocytes (IELs) (Verbeek et al., 2008, vanWanrooij et al., 2014). The cut-off of 20% aberrant IELs in the small bowel separates RCD Type I (<20%) vs. RCD Type II (RCD-II, 20% or greater). While RCD-I can be treated symptomatically with steroids, there are no approved or curative treatments for RCD-I and RCD-II, and the latter evolves to overt lymphoma in 50% of the cases, with very poor prognosis (Nijeboer et al., 2015).

Enteropathy-Associated T Cell Lymphoma (EATL) is a high-grade, systemic, T cell lymphoma almost exclusively seen as a complication of RCD-II (Nijeboer et al., 2015). Diagnosis includes imaging and histology to demonstrate the presence of malignant T cells in extra-epithelial locations such as lymph nodes or other organs. The treatment of EATL relies on surgical resection and chemotherapy, but the prognosis is very poor, with a 5-year survival of less than 20% (Nijeboer et al., 2015).

Some of the CD-associated symptoms experienced in response to ingestion of wheat are also reported by individuals who do not have the typical serologic, histologic, or genetic markers of CD, and who also do not experience the immunoglobulin E (IgE) serologic response associated with wheat allergy. The term non-celiac gluten sensitivity (NCGS) has been proposed to refer to the spectrum of conditions reported by these patients (Lundin and Alaedini, 2012). Non-celiac gluten sensitivity is currently understood as a condition associated with the experiencing of various symptoms in response to ingestion of foods containing wheat, rye, and barley, and the resolution of symptoms on removal of those foods from diet in individuals in whom CD and wheat allergy have been ruled out (Lundin and Alaedini, 2012).

As such, effective treatments for CD, NRCD, RCD, EATL and NCGS are urgently needed.

SUMMARY

In one aspect, the invention relates to a method of treating celiac disease or non-celiac gluten sensitivity in a subject in need thereof, comprising administering a therapeutically effective amount of an anti-IL-15 antibody or antigen-binding fragment thereof to the subject, wherein the therapeutically effective amount comprises 1-20 unit doses each administered at about 1-12 week intervals, each unit dose independently comprising about 50-1000 mg, preferably 75-600 mg, more preferably about 75 mg, about 150 mg, about 300 mg, about 450 mg or about 600 mg of the anti-IL-15 antibody or antigen-binding fragment thereof. In one embodiment, the therapeutically effective amount comprises 6 unit doses administered at about 2 week intervals. Each unit dose may be administered by subcutaneous injection or intravenous injection.

In another aspect, the invention relates to a pharmaceutical composition for the treatment of, or a pharmaceutical composition for use in a method of treating, celiac disease or non-celiac gluten sensitivity, comprising a therapeutically effective amount of an anti-IL-15 antibody or antigen-binding fragment thereof, wherein the therapeutically effective amount comprises 1-20 unit doses each to be administered at about 1-12 week intervals, each unit dose independently comprising about 50-1000 mg, preferably 75-600 mg, more preferably about 75 mg, about 150 mg, about 300 mg, about 450 mg or about 600 mg of the anti-IL-15 antibody or antigen-binding fragment thereof. In one embodiment of the pharmaceutical composition, the therapeutically effective amount comprises 6 unit doses to be administered at 2 week intervals. Each unit dose can be administered by subcutaneous injection or intravenous injection.

Another aspect of the invention relates to a method of treating refractory celiac disease in a subject in need thereof, comprising administering a therapeutically effective amount of an anti-IL-15 antibody or antigen-binding fragment thereof to the subject, wherein the therapeutically effective amount comprises 1-20 unit doses each administered at about 1-12 week intervals, each unit dose independently comprising about 1-50 mg/kg, preferably about 4-16 mg/kg, more preferably about 4 mg/kg, about 8 mg/kg, about 12 mg/kg or about 16 mg/kg of the anti-IL-15 antibody or antigen-binding fragment thereof. In one embodiment, the therapeutically effective amount comprises 6 unit doses administered at 2 week intervals, and an optional additional loading dose at week 1. Each unit dose is administered by subcutaneous injection or intravenous injection. The refractory celiac disease is type I or type II refractory celiac disease.

Also provided herein is a pharmaceutical composition for the treatment of, or a pharmaceutical composition for use in a method of treating, refractory celiac disease, comprising a therapeutically effective amount of an anti-IL-15 antibody or antigen-binding fragment thereof, wherein the therapeutically effective amount comprises 1-20 unit doses each administered at about 1-12 week intervals, each unit dose independently comprising about 1-50 mg/kg, preferably about 4-16 mg/kg, more preferably about 4 mg/kg, about 8 mg/kg, about 12 mg/kg or about 16 mg/kg of the anti-IL-15 antibody or antigen-binding fragment thereof. The therapeutically effective amount in some embodiments comprises 6 unit doses to be administered at 2 week intervals, and an optional additional loading dose to be administered at week 1. Each unit dose can be administered by subcutaneous injection or intravenous injection. The refractory celiac disease can be type I or type II.

In some embodiments of the methods and/or pharmaceutical compositions disclosed herein, the antibody may have a heavy chain variable region comprising one or more complementarity determining regions of SEQ ID NOs: 5-7, or a sequence having at least 80% sequence identity thereto. The antibody may, in certain embodiments, have a light chain variable region comprising one or more complementarity determining regions of SEQ ID NOs:8-10, or a sequence having at least 80% sequence identity thereto. The antibody in some embodiments has a heavy chain variable region comprising the amino acid sequence of SEQ ID NO:2, or a sequence having at least 80% sequence identity thereto. In certain embodiments, the antibody may have a light chain variable region comprising the amino acid sequence of SEQ ID NO:4, or a sequence having at least 80% sequence identity thereto.

DETAILED DESCRIPTION

Figure 1:
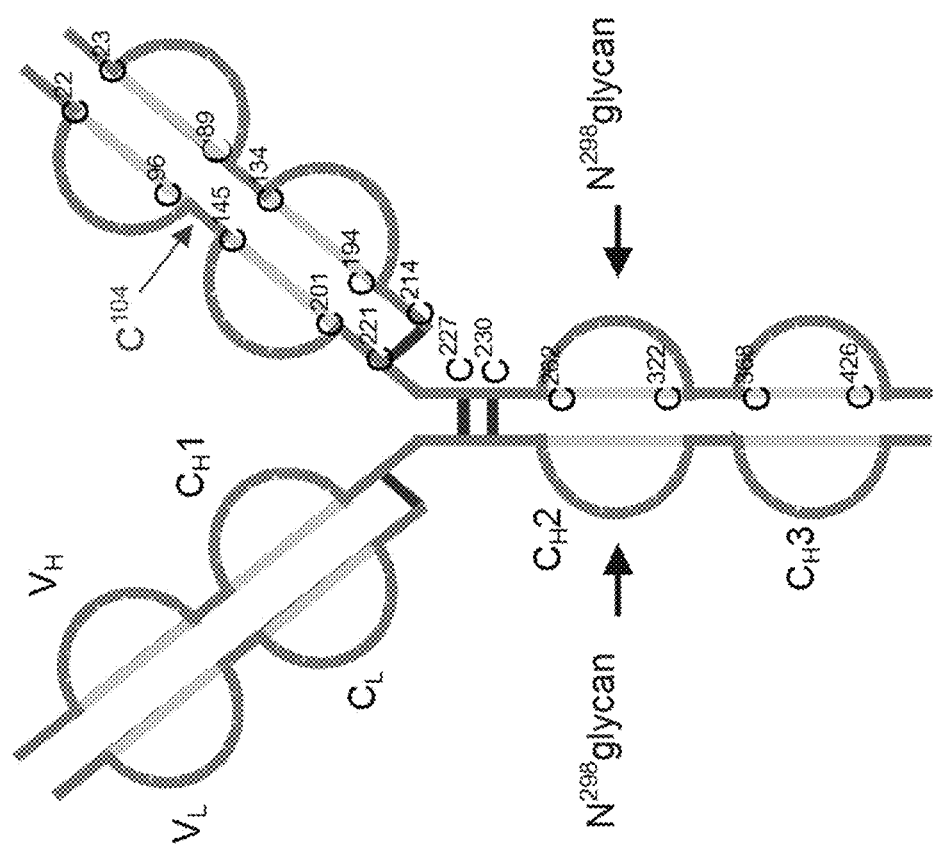
FIG. 1 illustrates a schematic structure of AMG 714.

The compositions and methods disclosed herein relate to the treatment of gastrointestinal disorders such as CD, NRCD, RCD, EATL and NCGS by modulating an activity of IL-15 using, e.g., a therapeutically effective amount of an IL-15 antagonist. In some embodiments, the IL-15 antagonist is an antibody. In some embodiments, IL-15 can be blocked by AMG 714, a monoclonal antibody which can bind to, and inhibit the function of IL-15.

Pharmaceutical compositions provided herein can include a therapeutically effective amount of a recombinant monoclonal antibody or antigen-binding fragments against IL-15, in particular human IL-15. Suitable antibodies can include, for example, murine, chimeric, humanized and fully human antibodies, as well as other antibody forms known in the art. In some embodiments, the antibody can include but is not limited to those disclosed in U.S. Pat. Nos. 7,247,304, 7,329,405, 7,153,507, 7,597,892, 7,585,961 and 8,345,105, all of which are incorporated herein by reference in their entirety. The antibody can be provided in the form of a recombinantly expressed glycoprotein, using methods disclosed in, e.g., International Patent Application No. WO2007/07087384, which is incorporated herein by reference in its entirety.

In one embodiment, the antibody is a fully human monoclonal antibody that binds IL-15. In a specific embodiment, the antibody is AMG 714 which has a heavy chain variable region comprising the amino acid sequence set forth in SEQ ID NO:2 and/or a light chain variable region comprising the amino acid sequence set forth in SEQ ID NO:4. The antibody can also have amino acid sequences of about 80%, 85%, 90%, 95% or greater identity to SEQ ID NO: 2 and/or SEQ ID NO: 4.

In some embodiments, the antibody can include a light chain variable region comprising one or more complementarity determining regions (CDRs) set forth in SEQ ID NOs:8-10, or homologous sequences thereof (e.g., having amino acid sequences of about 80%, 85%, 90%, 95% or greater identity to any of SEQ ID NOs: 8-10). The antibody can alternatively or additionally include a heavy chain variable region comprising one or more CDRs set forth in SEQ ID NOs:5-7, or homologous sequences thereof (e.g., having amino acid sequences of about 80%, 85%, 90%, 95% or greater identity to any of SEQ ID NOs: 5-7). In a particular embodiment, a human monoclonal antibody that binds IL-15 or an antigen-binding fragment thereof, includes a light chain variable region comprising all three CDRs set forth in SEQ ID NOs:8-10, or conservative amino acid substitutions thereof, and a heavy chain variable region comprising all three CDRs set forth in SEQ ID NOs: 5-7, or conservative amino acid substitutions thereof.

The pharmaceutical compositions disclosed herein can include a therapeutically effective amount of an isolated monoclonal antibody that binds IL-15 or an antigen-binding fragment thereof and a pharmaceutically acceptable carrier. The pharmaceutical compositions can be used to treat or prevent a disorder associated with an overexpression of human IL-15 and/or in which a down regulation or inhibition of human IL-15 induced effects is beneficial.

Also provided herein is a method of treating or preventing a disorder associated with an overexpression of human IL-15 and/or in which a down regulation or inhibition of human IL-15 induced effects is beneficial, by administering to a subject a therapeutically effective amount of an isolated anti-IL-15 antibody, or an antigen-binding fragment thereof.

Exemplary disorders that can be treated or prevented using the presently disclosed methods or compositions include, but are not limited to, Celiac Disease, Non-Responsive Celiac Disease, Refractory Celiac Disease, Enteropathy-Associated T Cell Lymphoma, and Gluten-Sensitive Enteropathy. Other disorders that can be treated include vasculitis, psoriasis, multiple sclerosis, rheumatoid arthritis (RA), inflammatory disorders (e.g., inflammatory bowel disease), allograft rejection, graft versus host disease, T-cell lymphoma, T-cell leukemia, cutaneous T cell lymphoma, dermatitis herpetiformis, HTLV-I-Associated Myelopathy/Tropical Spastic Paraparesis, alopecia areata, systemic juvenile rheumatoid arthritis, discoid lupus, myositis, endometriosis, Steven Johnson's Syndrome, eosinophilic esophagitis, and sarcoidosis.

Definitions

For convenience, certain terms employed in the specification, examples, and appended claims are collected here. Unless defined otherwise, all technical and scientific terms used herein have the same meaning as commonly understood by one of ordinary skill in the art to which this disclosure belongs.

The articles "a" and "an" are used herein to refer to one or to more than one (i.e., at least one) of the grammatical object of the article. By way of example, "an element" means one element or more than one element.

As used herein, the term "about" means within 20%, more preferably within 10% and most preferably within 5%. The term "substantially" means more than 50%, preferably more than 80%, and most preferably more than 90% or 95%.

The terms "IL-15," "IL-15 antigen" and "interleukin 15" are used interchangeably herein, and include any variants or isoforms thereof which are naturally expressed by cells. Interleukin 15 is a pro-inflammatory cytokine that serves as a potent growth, survival, and activation factor for T cells, particularly intestinal intraepithelial lymphocytes (IELs), and for natural killer (NK) cells. Increased expression of IL-15 has been demonstrated in a variety of inflammatory conditions, including CD, rheumatoid arthritis (RA), and psoriasis (Malamut et al., 2010). IL-15 is considered a central regulator of CD immunopathology and a non-redundant driver of lymphomagenesis in RCD. Inhibition of IL-15 by an antagonist is an attractive therapeutic target for the treatment of CD. Targeting of IL-15 by a fully human monoclonal antibody to bind IL-15 has served to elucidate the signaling mechanism facilitated by IL-15 in CD and has established experimental proof principle for the advantages of modulating downstream effectors of IL-15 (Malamut et al., 2010).

The term "antibody" as referred to herein includes whole antibodies and any antigen (e.g., IL-15) binding fragment (i.e., "antigen-binding portion") or single chain thereof. An "antibody" refers to a protein comprising at least two heavy (H) chains and two light (L) chains inter-connected by disulfide bonds, or an antigen binding portion thereof. Each heavy chain is comprised of a heavy chain variable region (abbreviated herein as VH) and a heavy chain constant region. The heavy chain constant region is comprised of three domains, CHL CH2 and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

It should be understood that the term "antibody" also includes various antibody modification and/or derivative forms, including without limitation, an anti-IL-15 antibody, or antigen-binding fragment thereof, coupled with or linked to an additional molecular entity, such as one or more different antibodies or antigen-binding fragments thereof (e.g., a bi-specific, tri-specific, or multi-specific), pharmaceutical agents, peptides or proteins, and detection agent or labels. The term "antibody" also includes single chain antibodies, diabodies, domain antibodies, nanobodies, and unibodies.

The terms "antigen-binding portion" and "antigen-binding fragment" of an antibody (or simply "antibody portion"), as used herein, refer to one or more fragments of an antibody that selectively bind to an antigen (e.g., IL-15). It has been shown that the antigen-binding function of an antibody can be performed by fragments of a full-length antibody. Examples of antigen-binding fragments encompassed within the term "antigen-binding portion" of an antibody include (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., Nature 341:544-546 (1989)), which consists of a VH domain; and (vi) an isolated complementarity determining region (CDR) or (vii) a combination of two or more isolated CDRs which may optionally be joined by a synthetic linker. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al., Science 242:423-426 (1988); and Huston et al., Proc. Natl. Acad. Sci. USA 85:5879-5883 (1988)). Such single chain antibodies are also intended to be encompassed within the terms "antigen-binding portion" and "antigen-binding fragment" of an antibody. These antibody fragments are obtained using conventional techniques known to those with skill in the art, and the fragments are screened for utility in the same manner as are intact antibodies.

The term "monoclonal antibody" as used herein, refers to an antibody which displays a single binding specificity and affinity for a particular epitope. Accordingly, the term "human monoclonal antibody" refers to an antibody which displays a single binding specificity and which has variable and constant regions derived from human germline immunoglobulin sequences. In one embodiment, human monoclonal antibodies are produced by a hybridoma which includes a B cell obtained from a transgenic non-human animal, e.g., a transgenic mouse, having a genome comprising a human heavy chain transgene and a light chain transgene fused to an immortalized cell. In another embodiment, human monoclonal antibodies can be produced by Chinese hamster ovary (CHO) cells.

The term "recombinant human antibody," as used herein, includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom, (b) antibodies isolated from a host cell (e.g., CHO cell) transformed to express the antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies have variable and constant regions derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

As used herein, a "heterologous antibody" is defined in relation to the transgenic non-human organism producing such an antibody. This term refers to an antibody having an amino acid sequence or an encoding nucleic acid sequence corresponding to that found in an organism not consisting of the transgenic non-human animal, and generally from a species other than that of the transgenic non-human animal.

An "isolated antibody," as used herein, refers to an antibody which is substantially free of other antibodies having different antigenic specificities (e.g., an isolated antibody that specifically binds to IL-15 is substantially free of antibodies that specifically bind antigens other than IL-15). An isolated antibody that specifically binds to an epitope of IL-15 may, however, have cross-reactivity to other related cytokines or to other IL-15 proteins from different species. However, the antibody preferably always binds to human IL-15. In addition, an isolated antibody is typically substantially free of other cellular material and/or chemicals. In a particular embodiment, a combination of "isolated" monoclonal antibodies having different IL-15 specificities are combined in a well-defined composition.

As used herein, "specific binding," "selective binding" and "selectively binds," refer to an antibody or a fragment thereof, binding to a predetermined antigen. For example, in one embodiment, the antibody binds with an affinity ($K_D$) of approximately less than $10^{-7}$ M, such as approximately less than $10^{-8}$ M, $10^{-9}$ M or $10^{-10}$ M or even lower when determined by surface plasmon resonance (SPR) technology in a BIACORE 3000 instrument using recombinant human IL-15 as the analyte and the antibody as the ligand, and binds to the predetermined antigen with an affinity that is at least two-fold greater than its affinity for binding to a non-specific antigen (e.g., BSA, casein) other than the predetermined antigen or a closely-related antigen. The phrases "an antibody recognizing an antigen" and "an antibody specific for an antigen" are used interchangeably herein with the term "an antibody which selectively binds to an antigen."

The term "$K_D$," as used herein, is intended to refer to the dissociation equilibrium constant of a particular antibody-antigen interaction.

The term "nucleic acid molecule," as used herein, refers to DNA and RNA molecules. A nucleic acid molecule may be single-stranded or double-stranded, but preferably is double-stranded DNA.

The term "isolated nucleic acid molecule," as used herein in reference to nucleic acids encoding antibodies or antibody portions (e.g., VU, VL, CDR3) that selectively bind to IL-15, refer to a nucleic acid molecule in which the nucleotide sequences encoding the antibody or antibody portion are free of other nucleotide sequences encoding antibodies or antibody portions that bind antigens other than IL-15, which other sequences may naturally flank the nucleic acid in human genomic DNA.

In one embodiment, the human anti-IL-15 antibody can have a heavy chain variable region (VH) encoded by the nucleotide sequence set forth in SEQ ID NO: 1, or conservative nucleic acid substitutions (e.g., silent mutation) thereof, and/or a light chain variable region (VL) encoded by the nucleotide sequence set forth in SEQ ID NO: 3, or conservative nucleic acid substitutions thereof. The antibody can also have VH and VL's encoded by nucleotide sequences having about 80%, 85%, 90%, 95% or greater identity to SEQ ID NO: 1 and/or SEQ ID NO: 3, respectively.

In one embodiment, the antibody can have a heavy chain variable region comprising the amino acid sequence set forth in SEQ ID NO: 2, or conservative amino acid substitutions thereof, and/or a light chain variable region comprising the amino acid sequence set forth in SEQ ID NO:4, or conservative amino acid substitutions thereof. The antibody can also have amino acid sequences of about 80%, 85%, 90%, 95% or greater identity to SEQ ID NO: 2 and/or SEQ ID NO: 4.

In some embodiments, the antibody can include a light chain variable region comprising one or more complementarity determining regions (CDRs) set forth in SEQ ID NOs: 8-10, or homologous sequences thereof (e.g., having amino acid sequences of about 80%, 85%, 90%, 95% or greater identity to any of SEQ ID NOs: 8-10, or having 1 or 2 or 3 or 4 amino acid substitutions or changes thereto). The antibody can alternatively or additionally include a heavy chain variable region comprising one or more CDRs set forth in SEQ ID NOs: 5-7, or homologous sequences thereof (e.g., having amino acid sequences of about 80%, 85%, 90%, 95% or greater identity to any of SEQ ID NOs: 5-7, or having 1 or 2 or 3 or 4 amino acid substitutions or changes thereto). In a particular embodiment, a human monoclonal antibody that binds IL-15 or an antigen-binding fragment thereof, includes a light chain variable region comprising all three CDRs set forth in SEQ ID NOs: 8-10, or conservative amino acid substitutions thereof, and a heavy chain variable region comprising all three CDRs set forth in SEQ ID NOs: 5-7, or conservative amino acid substitutions thereof.

One embodiment of the present invention also encompasses "conservative sequence modifications" or "conservative sequence substitutions" of the sequences set forth in SEQ ID NOs: 1-10, i.e., nucleotide and amino acid sequence modifications which do not significantly affect or alter the binding characteristics of the antibody encoded by the nucleotide sequence or containing the amino acid sequence. Such conservative sequence modifications include nucleotide and amino acid substitutions, additions and deletions. Modifications can be introduced into SEQ ID NOs: 1-10 by standard techniques known in the art, such as site-directed mutagenesis and PCR-mediated mutagenesis. Conservative amino acid substitutions include ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, a predicted nonessential amino acid residue in a human anti-IL-15 antibody is preferably replaced with another amino acid residue from the same side chain family.

Alternatively, in another embodiment, mutations can be introduced randomly along all or part of an anti-IL-15 antibody coding sequence, such as by saturation mutagenesis, and the resulting modified anti-IL-15 antibodies can be screened for binding activity.

Accordingly, antibodies encoded by the (heavy and light chain variable region) nucleotide sequences disclosed herein and/or containing the (heavy and light chain variable region) amino acid sequences disclosed herein (i.e., SEQ ID NOs: 1-4) include substantially similar antibodies encoded by or containing similar sequences, which have been conservatively modified. Further, discussion as to how such substantially similar antibodies can be generated based on the partial (i.e., heavy and light chain variable regions) sequences disclosed herein as SEQ ID Nos:1-4 is provided below.

For nucleic acids, the term "substantial homology" indicates that two nucleic acids, or designated sequences thereof, when optimally aligned and compared, are identical, with appropriate nucleotide insertions or deletions, in at least about 80% of the nucleotides, usually at least about 90% to 95%, and more preferably at least about 98% to 99.5% of the nucleotides. Alternatively, substantial homology exists when the segments will hybridize under selective hybridization conditions, to the complement of the strand.

For amino acid sequences, the term "homology" indicates the degree of identity between two amino acid sequences when optimally aligned and compared with appropriate insertions or deletions.

The percent identity between two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm.

The percent identity between two nucleotide sequences can be determined using the GAP program in the GCG software package (available at www.gcg.com), using a NWSgapdna. CMP matrix and a gap weight of 40, 50, 60, 70, or 80 and a length weight of 1, 2, 3, 4, 5, or 6. The percent identity between two nucleotide or amino acid sequences can also be determined using the algorithm of E. Meyers and W. Miller (CABIOS, 4:11-17 (1989)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (J. Mol. Biol. (48):444-453 (1970)) algorithm which has been incorporated into the GAP program in the GCG software package (available at www.gcg.com), using either a Blossum 62 matrix or a PAM250 matrix, and a gap weight of 16, 14, 12, 10, 8, 6, or 4 and a length weight of 1, 2, 3, 4, 5, or 6.

The nucleic acid and protein sequences of the present invention can further be used as a "query sequence" to perform a search against public databases to, for example, identify related sequences. Such searches can be performed using the NBLAST and)(BLAST programs (version 2.0) of Altschul, et al., J. Mol. Biol. 215:403-10 (1990). BLAST nucleotide searches can be performed with the NBLAST program, score=100, wordlength=12 to obtain nucleotide sequences homologous to the nucleic acid molecules of the invention. BLAST protein searches can be performed with the)(BLAST program, score=50, wordlength=3 to obtain amino acid sequences homologous to the protein molecules of the invention. To obtain gapped alignments for comparison purposes, Gapped BLAST can be utilized as described in Altschul et al., Nucleic Acids Res. 25(17):3389-3402 (1997). When utilizing BLAST and Gapped BLAST programs, the default parameters of the respective programs (e.g.,)(BLAST and NBLAST) can be used. (See www.ncbi.nlm.nih.gov).

As used herein, the term "subject" includes any human or non-human animal. For example, the methods and compositions of the present invention can be used to treat a subject having an inflammatory disease, such as celiac disease, Refractory Celiac Disease, Enteropathy-Associated T Cell Lymphoma and Non-celiac gluten sensitivity. The term "non-human animal" includes all vertebrates, e.g., mammals and non-mammals, such as non-human primates, sheep, dog, cow, chickens, amphibians, reptiles, etc.

A "therapeutically effective dosage" or "therapeutically effective amount" for inflammatory disorders, such as Celiac Disease, Refractory Celiac Disease, Gluten-Sensitive Enteropathy and/or Enteropathy-Associated T Cell Lymphoma, or the like, will preferably result in an improvement of patient's clinical outcome or otherwise ameliorate signs and/or symptoms in a subject. For example, a therapeutically effective dosage of AMG-714 can result in improved clinical outcomes and/or improve laboratory test results of patients receiving treatment, for example the parameters to be monitored in clinical trials and/or physician assessments, as set forth herein.

A "unit dose" refers to an amount of pharmaceutical composition, in particular the active ingredient therein (e.g., an anti-IL-15 antibody such as AMG 714) that is administered to a subject in one treatment session. A treatment session may be continuous, e.g., uninterrupted parenteral administration (e.g., subcutaneous or intravenous) of a single bolus for a duration of time (e.g., 1 hour, 2 hours). A treatment session can also be divided into two or more subsections, such that one unit dose is administered over time (e.g., 12 hours, 24 hours) with each bolus followed by a break or recovery time.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the antibody may be coated in a material to protect the compound from the action of acids and other natural conditions that may inactivate the compound.

A "pharmaceutically acceptable salt" refers to a salt that retains the desired biological activity of the parent compound and does not impart any undesired toxicological effects (see e.g., Berge, S. M., et al., J. Pharm. Sci. 66:1-19 (1977)). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

Various aspects of the present invention are described in further detail in the following subsections.

Pharmaceutical Compositions and Preparations Thereof

The present invention includes, in one aspect, a pharmaceutical composition having a therapeutically effective amount of a therapeutic antibody or an antigen-binding fragment thereof (e.g., a human monoclonal antibody that binds IL-15 or an antigen-binding fragment thereof), which can be formulated together with a pharmaceutically acceptable carrier.

In some embodiments, AMG 714, a fully human immunoglobulin (IgG1κ) monoclonal antibody (mAb) that binds to interleukin 15 (IL-15), is useful as a treatment for, e.g., celiac disease, gluten-free diet (GFD) non-responsive celiac disease (NRCD), non-celiac gluten sensitivity and Type II refractory celiac disease (RCD-II).

Interleukin 15 (IL-15), a glycoprotein of approximately 14-15 kDa, is a pro-inflammatory cytokine with structural similarities to IL-2. IL-15 exerts biological effects on many immunologically relevant cells (Fehniger and Caligiuri, 2001). While important differences are present across species, IL-15 generally acts as a development, homeostasis, and activation factor for NK cells and memory phenotype CD8+ T cells, including IELs. It also induces the production of chemokines and cytokines by these cell types. IL-15 potently stimulates the production of pro-inflammatory cytokines such as IL-1, IL-6, and TNF-α by monocytes/macrophages. IL-15 produced by follicular dendritic cells is known to support germinal center B cell proliferation and immunoglobulin class switching (Park et al., 2004; Litinskiy et al., 2002). Targeted disruption of either the IL-15 or IL-15Rα genes in mice has been shown to result in the loss of NK, NK-T, T cell receptor gamma delta (TCRγδ+) IELs, and memory CD8+ T cells (Lodolce et al., 1998). In IL-15 knockout mice, these defects are reversible by the administration of exogenous IL-15 (Kennedy et al., 2000). However, human NK cells are not entirely dependent on IL-15 (Lebrec et al., 2013).

IL-15 messenger RNA (mRNA) is expressed in a wide variety of tissues and cell types. However, expression of IL-15 protein is much more restricted and is subject to multiple post-transcriptional control mechanisms. Sources of IL-15 protein include monocytes, macrophages, epithelial and fibroblastic cells, and bone marrow stromal cells (Fehniger and Caligiuri, 2001). IL-15 and its receptor are also expressed in some organs outside the immune system; the role of IL-15 in these systems is less well understood. The absence of any overt defects outside the immune system in IL-15 and IL-15Rα knockout mice suggests that IL-15 may not be essential in any other system.

IL-15 binds to a heterotrimeric receptor that consists of a β chain that is shared with the IL-2 receptor (CD122 or IL-2/IL-15Rβ), the common γ chain (γC) shared with IL-2, -4, -7, -9, and -21 receptors, and a unique α chain. IL-15 binds with high affinity to the IL-15Rα chain, which then interacts with the IL-2/IL-15Rβ and the γC. The association of the IL-15/IL-15Rα complex with the other two components of the complete receptor complex can occur in a cis configuration, in which all three receptor components are present on the same cell, or in a trans configuration, in which the IL-15/IL-15Rα pair is on one cell and the receptor β and γC chains are on another (Schluns et al., 2005). IL-15 can also associate with IL-15Rα on the cell surface and then be cleaved into soluble cytokine/receptor complexes that have the potential to stimulate CD8+ T cells and NK cells (Anthony et al., 2015).

Increased expression of IL-15 has been demonstrated in a variety of inflammatory conditions, including RA, psoriasis, inflammatory bowel disease, graft-versus-host disease, solid organ transplant rejection (Blaser et al., 2005; Conti et al., 2003; Gianfrani et al., 2005; McInnes and Gracie, 2004), and celiac disease (Gianfrani et al., 2005; Meresse et al., 2012).

AMG 714, a fully human immunoglobulin (IgG1κ) monoclonal antibody, binds to and inhibits the function of IL-15 in all its known forms (cis, trans, soluble IL-15 bound to IL-15 receptor alpha (IL-15Ra)). AMG 714 inhibits IL-15-induced T cell proliferation and shows a dose-dependent inhibition of IL-15-induced tumor necrosis factor alpha (TNF-α) production. The structure of AMG 714 is illustrated in FIG. 1.

AMG 714 can be produced by any antibody production methods generally known in the art. For example, AMG 714 may be produced from a B cell hybridoma cell line. AMG 714 can also be produced by a mammalian cell line such as Chinese hamster ovary (CHO) cell line. As one of ordinary skill in the art would understand, the heavy chain C-terminal lysine can be absent from the version produced by CHO cells (Dick Jr. et al., Biotechnol. Bioeng. 2008; 100: 1132-1143).

In nonclinical experiments, AMG 714 was found to recognize an epitope that is essential for the interaction between human IL-15 (hIL-15) and its receptor complex. AMG 714 showed a dose-dependent inhibition of IL-15-induced proliferation of peripheral blood T cells and cell lines expressing IL-15 receptors, as well as a dose-dependent inhibition of hIL-15-induced TNF-α production. AMG 714 was found to be efficacious in a mouse model of celiac disease triggered by the transgenic expression of human IL-15 in the gut epithelium. In this model, AMG 714 prevented IEL activation and proliferation, as well as histological abnormalities. In addition, AMG 714 was able to induce apoptosis of human IELs in ex vivo culture of small intestinal explants from patients with active celiac disease and RCD-II.

Due to low binding potency of AMG 714 for macaque IL-15, the safety profile of AMG 714 has been evaluated in nonclinical studies in non-human primates (NHPs), specifically cynomolgus monkeys, using the surrogate molecule Hu714MuXHu. In NHPs, the inhibition of IL-15 by Hu714MuXHu resulted in reversible NK cell reduction and associated gastrointestinal infections in some animals; however, NK cell depletion has not been observed in humans (Lebrec et al., 2013) and no corresponding gastroenteritis or enteric infections have been reported as a frequent adverse event (AE) in human studies. No other toxicology signals have been observed. The difference between this observation and the NK cell depletion seen in NHPs appears to be related to a difference between human and cynomolgus monkey in the sensitivity of NK cells to IL-15 blockade. Human NK cells are not dependent on IL-15 for their survival, possibly due to the redundant role of IL-2 on human NK cells.

Approximately 200 subjects have been exposed to AMG 714 to date for the treatment of RA and psoriasis, including approximately 140 subjects for 12 weeks of biweekly dosing. AMG 714 has been studied in four clinical trials, including one Phase 1 study in NHV (30 subjects on AMG 714, 10 on placebo, intravenous [IV] and subcutaneous [SC]), one Phase 1 study in RA (29 subjects on AMG 714, no placebo, IV), a Phase 1b/2a in psoriasis (14 patients on AMG 714, 6 on placebo, SC), and a Phase 2b study in RA (121 subjects on AMG 714, 58 on placebo, SC). To date, AMG 714 has been well tolerated and its safety profile has been generally comparable to placebo with the exception of injection site reactions, which were more commonly reported in subjects exposed to AMG 714. AMG 714 has not been shown to induce NK cell loss.

In RA clinical trials, AMG 714 demonstrated a response in approximately 60% of patients in both Phase 1 and Phase 2 studies versus a response of approximately 30% in the placebo group. AMG 714 also led to decreases in inflammatory biomarkers such as C-reactive protein (CRP) and erythrocyte sedimentation rate (ESR). AMG 714 did not demonstrate a response in clinical trials with psoriasis patients, suggesting AMG 714's action is selective, unlike that of broad systemic immune suppressants.

AMG 714 has a PK profile consistent with a typical human immunoglobulin GI antibody with no apparent target-mediated disposition and a half-life of 20 to 22 days. Immunogenicity of AMG 714 has been reported in only one blood sample from one subject in the RA and psoriasis clinical program.

Pharmaceutical compositions of the present invention also can be administered in combination therapy, i.e., combined with other agents. For example, the combination therapy can include a composition of the present invention with at least one or more additional therapeutic agents, such as anti-inflammatory agents, DMARDs (disease-modifying anti-rheumatic drugs), immunosuppressive agents, chemotherapeutics, and psoriasis agents. The pharmaceutical compositions of the invention can also be administered in conjunction with radiation therapy. Co-administration with other antibodies, such as CD4 specific antibodies and IL-2 specific antibodies, are also encompassed by the invention. Such combinations with CD4 specific antibodies or IL-2 specific antibodies are considered particularly useful for treating autoimmune diseases and transplant rejections.

A composition of the present invention can be administered by a variety of methods known in the art. As will be appreciated by the skilled artisan, the route and/or mode of administration will vary depending upon the desired results. The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are generally known to those skilled in the art. See, e.g., Sustained and Controlled Release Drug Delivery Systems, J. R. Robinson, ed., Marcel Dekker, Inc., New York, 1978.

To administer a compound of the invention by certain routes of administration, it may be necessary to coat the compound with, or co-administer the compound with, a material to prevent its inactivation. For example, the compound may be administered to a subject in an appropriate carrier, for example, liposomes, or a diluent. Pharmaceutically acceptable diluents include saline and aqueous buffer solutions. Liposomes include water-in-oil-in-water CGF emulsions as well as conventional liposomes (Strejan et al., J. Neuroimmunol. 7:27 (1984)).

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

Dosage regimens can be adjusted to provide the optimum desired response (e.g., a therapeutic response). For example, a single bolus may be administered, several divided doses may be administered over time or the dose may be proportionally reduced or increased as indicated by the exigencies of the therapeutic situation. For example, the human antibodies of the invention may be administered once or twice weekly by subcutaneous injection or once or twice monthly by subcutaneous injection.

It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

For the therapeutic compositions, formulations of the present invention include those suitable for oral, nasal, topical (including buccal and sublingual), rectal, vaginal and/or parenteral administration. The formulations may conveniently be presented in unit dose form and may be prepared by any methods known in the art of pharmacy. The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred percent, this amount will range from about 0.001 percent to about ninety percent of active ingredient, preferably from about 0.005 percent to about 70 percent, most preferably from about 0.01 percent to about 30 percent.

Dosage forms for the topical or transdermal administration of compositions of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

When the compounds of the present invention are administered as pharmaceuticals, to humans and animals, they can be given alone or as a pharmaceutical composition containing, for example, 0.001 to 90% (more preferably, 0.005 to 70%, such as 0.01 to 30%) of active ingredient in combination with a pharmaceutically acceptable carrier.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. In some embodiments, subcutaneous and/or intravenous administration can be used, certain advantages and disadvantages of which are summarized below.

| Administration form | Advantages | Challenges |
|---|---|---|
| Subcutaneous (SC) | shorter clinic/office visits for the patient optimized use of resources self-administration is possible less invasive than IV administration | pain-free administration of larger fluid volumes minimization of adverse events at the injection site guarantee of good absorption and bioavailability administration of exact doses requires practice |

-continued

| Administration form | Advantages | Challenges |
|---|---|---|
| Intravenous (IV) | suitable for substances that can cause irritations suitable for drugs that must be administered in larger volumes | requires trained personnel in special infusion settings handling of port system (e.g., central port, Hickman catheter, PICC) placement of aperipheral cannula longer clinic/office stays than with SC administration risk of systemic infections |

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts. A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved. In general, a suitable daily dose of a composition of the invention will be that amount of the compound which is the lowest dose effective to produce a therapeutic effect. Such an effective dose will generally depend upon the factors described above. It is preferred that administration be intravenous, intramuscular, intraperitoneal, or subcutaneous, preferably administered proximal to the site of the target. If desired, the effective daily dose of a therapeutic composition may be administered as two, three, four, five, six or more sub-doses administered separately at appropriate intervals throughout the day, optionally, in unit dose forms. While it is possible for a compound of the present invention to be administered alone, it is preferable to administer the compound as a pharmaceutical formulation (composition).

Therapeutic compositions can be administered with medical devices known in the art. For example, in a preferred embodiment, a therapeutic composition of the invention can be administered with a needleless hypodermic injection device, such as the devices disclosed in U.S. Pat. Nos. 5,399,163, 5,383,851, 5,312,335, 5,064,413, 4,941,880, 4,790,824, or 4,596,556. Examples of well-known implants and modules useful in the present invention include: U.S. Pat. No. 4,487,603, which discloses an implantable microinfusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. Many other such implants, delivery systems, and modules are known to those skilled in the art.

The therapeutic antibodies of the present invention can be formulated to aid in proper distribution in vivo. For example, the blood-brain barrier (BBB) excludes many highly hydrophilic compounds. To aid therapeutic compounds of the invention in crossing the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., V. V. Ranade J. Clin. Pharmacol. 29:685 (1989). Exemplary targeting moieties include folate or biotin (see, e.g., U.S. Pat. No. 5,416,016 to Low et al.); mannosides (Umezawa et al., Biochem. Biophys. Res. Commun. 153:1038 (1988)); antibodies (P. G. Bloeman et al., FEBS Lett. 357:140 (1995); M. Owais et al., Antimicrob. Agents Chemother. 39:180 (1995)); surfactant protein A receptor (Briscoe et al., Am. J. Physiol. 1233:134 (1995)), different species of which may comprise the formulations of the inventions, as well as components of the invented molecules; p120 (Schreier et al., J. Biol. Chem. 269:9090 (1994)); see also K. Keinanen; M. L. Laukkanen FEBS Lett. 346:123 (1994); J. J. Killion; I. J. Fidler Immunomethods 4:273 (1994). The therapeutic compounds of the present invention can be formulated in liposomes; and the liposomes can include a targeting moiety. The therapeutic compounds formulated in liposomes can be delivered by bolus injection to a site proximal to a tumor or infection. The composition must be fluid to the extent that the composition can be easily drawn into a syringe. The liposome composition can be stable under the conditions of manufacture and storage. The liposome composition can be preserved against the contaminating action of microorganisms such as bacteria and fungi.

The composition of the present invention can be formulated to prevent or reduce the transport across the placenta. This can be done by methods known in the art, e.g., by PEGylation of the antibody or by use of F(ab)2' fragments. Further references can be made to "Cunningham-Rundles C, Zhuo Z, Griffith B, Keenan J. (1992) Biological activities of polyethylene-glycol immunoglobulin conjugates." Resistance to enzymatic degradation. J Immunol Methods. 152: 177-190; and to Landor M. (1995) Maternal-fetal transfer of immunoglobulins, Ann Allergy Asthma Immunol 74:279-283.

The composition must be sterile and fluid to the extent that the composition is deliverable by syringe. In addition to water, the carrier can be an isotonic buffered saline solution, ethanol, polyol (for example, glycerol, propylene glycol, and liquid polyetheylene glycol, and the like), and suitable mixtures thereof. Proper fluidity can be maintained, for example, by use of coating such as lecithin, by maintenance of required particle size in the case of dispersion and by use of surfactants. In many cases, it is preferable to include isotonic agents, for example, sugars, polyalcohols such as mannitol or sorbitol, and sodium chloride in the composition. Long-term absorption of the injectable compositions can be brought about by including in the composition an agent which delays absorption, for example, aluminum monostearate or gelatin.

When the active compound is suitably protected, as described above, the compound may be orally administered, for example, with an inert diluent or an assimilable edible carrier.

Use of the Pharmaceutical Composition to Treat Celiac Disease and Non-Celiac Gluten Sensitivity Celiac disease is a systemic autoimmune disease triggered by gluten consumption in genetically susceptible individuals (Green and Cellier, 2007). Currently ~1% of the United States (US) and European Union (EU) populations are affected by celiac disease, albeit only 10-20% of celiac patients are diagnosed. Celiac was the first autoimmune disease with an identified antigen: gluten, the main protein present in some of the most common cereals (e.g., wheat, barley, rye). Modern diets are increasingly enriched with gluten and it is also used as an additive in processed foods, cosmetics, and oral medications. Gluten is the second most common food ingredient after sugar and, in some countries, is present in up to 80% of foodstuff.

Humans lack enzymes to fully digest gluten, which, in the right genetic context (i.e., the presence of HLA-DQ2/8, Th1-prone immune system), triggers inflammation and autoimmunity in the gut and other organs following deamidation by the enzyme transglutaminase (tTG), which itself becomes a target for auto-antibodies. IL-15 is believed to be a key mediator in both the adaptive immune response, leading to extra-intestinal manifestations, and the innate immune response mediated through intra-epithelial lymphocytes (IELs), leading to intestinal mucosal atrophy and gastrointestinal symptoms.

Figure 2:
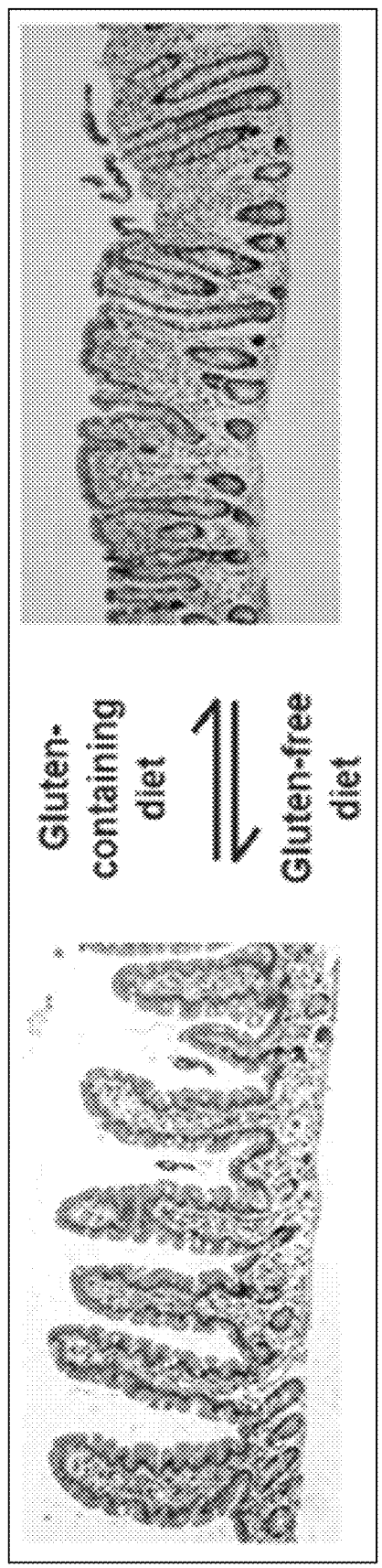
FIG. 2 illustrates villi present in the gut of healthy subject and subjects with active celiac disease.

Celiac disease causes debilitating symptoms and potentially serious medical complications. In many patients, gastrointestinal symptoms derived from the increase in inflammatory cytokine-producing IELs and the gut mucosal damage dominate the patient-reported symptoms at diagnosis. As illustrated in FIG. 2, the normal villi (absorptive finger-like prolongations) present in the gut of healthy individuals (left) are lost in active celiac disease (right) as a result of mucosal atrophy and crypt enlargement. The ratio of the villous height (VH) to the intestinal crypt depth (CD), the VH:CD ratio, is one of the main descriptors of the severity of celiac disease (Taavela et al., 2013). Small bowel damage often leads to nutrient malabsorption that can result in a range of further clinical manifestations (e.g., anemia, osteopenia, failure to thrive in children). In addition, extra-intestinal symptoms and systemic manifestations are often present, such as dermatitis, infertility, neurological disorders, and skeletal disorders (Green and Cellier, 2007).

Despite this considerable morbidity, celiac disease is the only common autoimmune disorder with no approved medication. Currently, the only available strategy for the management of celiac disease is a lifelong total avoidance of gluten. While simple in theory, in practice, the ubiquity of gluten in foodstuffs, medications, household substances, cosmetics, and even gluten-free items makes total avoidance of gluten difficult, if not impossible.

The main challenge to the successful maintenance of a gluten free diet (GFD) is that cereal flours are widely used in the food industry and are present in most food products either naturally or as additives. Although gluten-free products can be purchased, commercially manufactured gluten-free products may be difficult to find, tend to be less flavorful, and are more expensive than regular gluten-containing foods, which can sometimes deter patients from adhering to a GFD. In addition, many countries are deficient in the appropriate labeling of food products. Even in countries with superior labeling guidelines, foods labeled "gluten-free" may nevertheless contain gluten. For example, in northern European countries, gluten amounts of up to 100 parts per million (ppm) are permitted in gluten-free products designated for celiac sufferers (Gibert et al., 2006).

For these reasons, celiac sufferers are regularly exposed to gluten contamination when consuming food and beverages. This exposure to gluten contamination and the associated physiological and psychological consequences result in a self-limitation of social activities and/or a reduction in the variety of foods consumed. Thus, a GFD presents both a considerable challenge and substantial burden for patients. A study by Shah et al., (2014) found that the burden of celiac disease and a GFD on patients' quality of life was ranked second only to end-stage renal disease, a condition that requires multiple weekly dialysis treatments.

As discussed above, the ubiquitous presence of gluten makes total avoidance very difficult, if not impossible. As little as 50 mg/day (a normal diet contains greater than 10 g/day) triggers activation of T cells in the small bowel and causes intestinal mucosal damage (Catassi et al., 2007). For this reason, more than 50% of celiac patients on a GFD continue to present with active disease and intestinal immune activation and mucosal atrophy (Lee et al., 2003; Cranney et al., 2007; Hopper et al., 2007; Midhagen et al., 2003).

Patients who continue to have symptoms despite attempting to maintain a GFD are deemed to have NRCD. NRCD has been defined as "persistent symptoms, signs or laboratory abnormalities typical of celiac disease, despite 6-12 months of dietary gluten avoidance" (Rubio-Tapia et al., 2013). Patient support groups and experts agree that alternative treatment options independent of, or in combination with, GFD are urgently needed to improve the quality of life for celiac patients.

Figure 5:
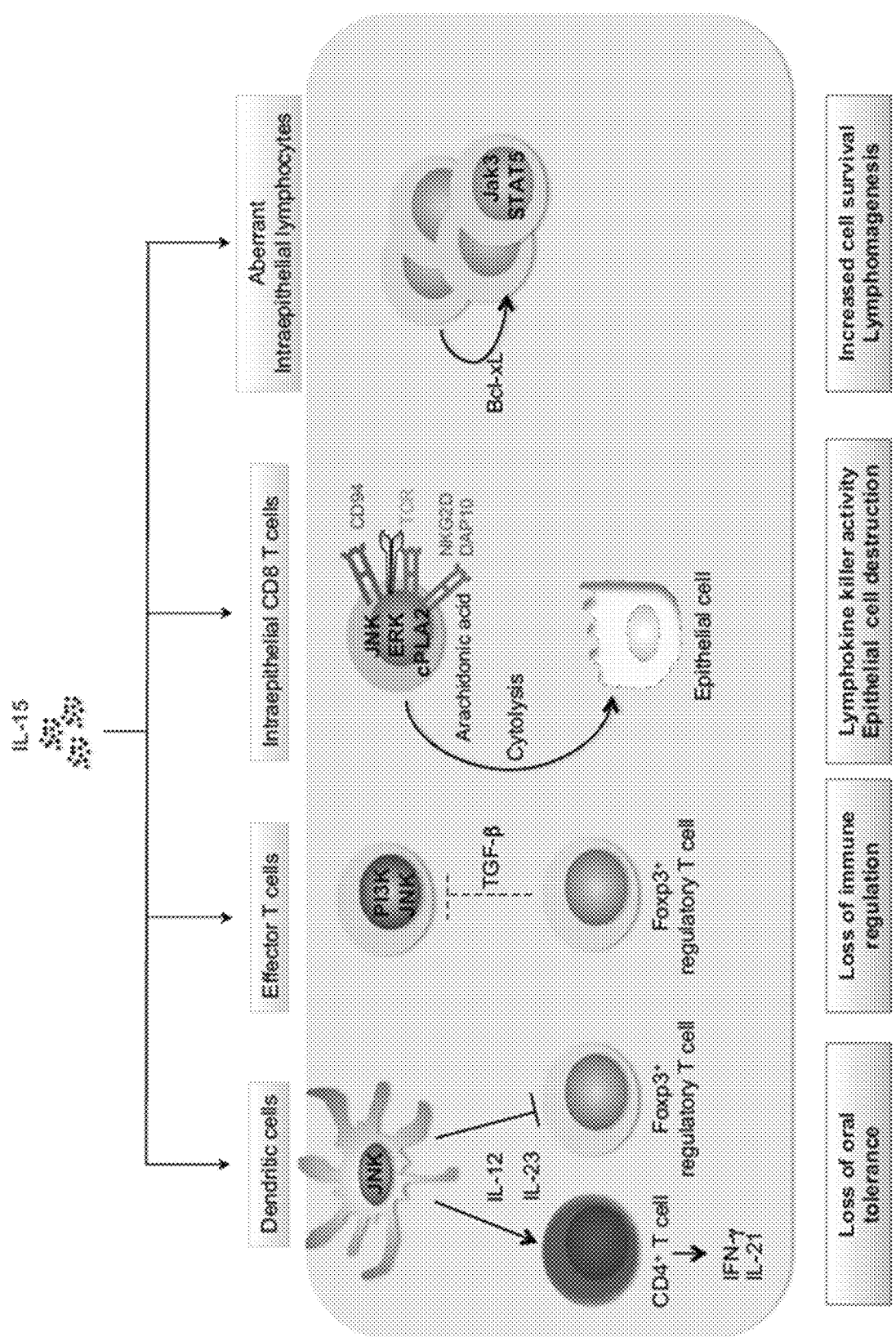
FIG. 5 illustrates a simplified schematic of the multiple roles of IL-15 in celiac and refractory celiac disease.

Substantial experimental data support multiple actions of IL-15 in the pathophysiology of CD and RCD (Abadie and Jabri et al., 2014) as illustrated in FIG. 5. For example, within the innate immune response IL-15 is an essential, non-redundant growth and activation factor for the IELs which destroy the intestinal mucosa. Further, the expression of IL-15 in the intestinal epithelium is necessary for villous atrophy. Additionally, in some patients, IL-15 drives progression towards lymphomagenesis and potentially fatal RCD-II (Malamut et al., 2010).

Experimental data suggest IL-15 mediates the adaptive immune response as well. For example, IL-15 enhances the presentation of deamidated gluten peptides (DGP) by antigen-presenting cells (APCs). Further, IL-15 renders the activated CD4+ T cells resistant to inhibition by regulatory T cell.

By activating the IELs, IL-15 is believed to be the main mediator in the mucosal damage that ensues in response to gluten exposure in celiac disease (Korneychuk et al., 2014). The expression of IL-15 in the intestinal epithelium is necessary for villous atrophy in animal models of celiac disease and circumstantial evidence suggests this to be the case in humans as well. In addition, IL-15 renders effector T cells resistant to inhibition by regulatory T cells ($T_{reg}$) (Abadie and Jabri 2014), promoting the loss of tolerance to food antigens (DePaolo et al., 2011; Korneychuk et al., 2014).

One of the mouse models of celiac disease is an IL-15-transgenic mouse, in which IL-15 overexpression by gut epithelial cells leads to celiac-like presentations, including T and B cell-mediated pathology (Yokoyama et al., 2009 and 2011). IEL apoptosis has been observed in this animal model after treatment with the anti-IL-15 mAb AMG 714 (Malamut et al., 2010) or anti-IL-15R mAbs (Yokoyama et al., 2009). IL-15 has been proven to be a key factor in the loss of tolerance to food antigens (DePaolo et al., 2011; Korneychuk, et al., 2014).

Some of the CD-associated symptoms experienced in response to ingestion of wheat are also reported by individuals who do not have the typical serologic, histologic, or genetic markers of CD, and who also do not experience the immunoglobulin E (IgE) serologic response associated with wheat allergy. The term Non-celiac gluten sensitivity or non-celiac gluten sensitivity (NCGS) has been proposed to refer to the spectrum of conditions reported by these patients (Lundin and Alaedini, 2012). Non-celiac gluten sensitivity is currently understood as a condition associated with the experiencing of various symptoms in response to ingestion of foods containing wheat, rye, and barley, and the resolution of symptoms on removal of those foods from diet in individuals in whom CD and wheat allergy have been ruled out (Lundin and Alaedini, 2012). The symptoms may be accompanied with an increase in levels of antibody to gluten. The majority of symptoms associated with NCGS are subjective, including abdominal pain, headache, "brain fog," tingling and/or numbness in hands and feet, fatigue, and musculoskeletal pain. However, other symptoms such as rash and diarrhea, as well as more severe neurologic and psychiatric conditions including schizophrenia and cerebellar ataxia, have also been reported to be associated with NCGS.

The present invention provides methods and compositions for treating celiac disease or non-celiac gluten sensitivity by administering a therapeutically effective amount of an anti-IL-15 antibody or antigen-binding fragment thereof disclosed herein. In some embodiments, a therapeutically effective amount of the anti-IL-15 antibody or antigen-binding fragment thereof can achieve, e.g., for the treatment of CD or NCGS one or more of, (1) attenuation of gluten-induced small intestinal mucosal morphological injury, (2) reduction of villous height to crypt depth (VH:CD) ratio, (3) attenuation of gluten-induced small intestinal mucosal inflammation measured as intraepithelial lymphocyte (IELs) density, (4) attenuation of gluten-induced small intestinal mucosal morphological injury using a grouped classification of Marsh score, (5) attenuation of gluten-induced serum antibodies by measuring of anti-tissue transglutaminase antibodies (anti-tTG IgA) and anti-deamidated gliadin peptide (anti-DGP) IgA and IgG, and/or (6) attenuation of gluten-induced clinical symptoms as assessed by the Celiac Disease Patient-Reported Outcome (CeD PRO), the Bristol Stool Form Scale (BSFS), the Gastrointestinal Symptom Rating Scale (GSRS) and celiac disease GSRS (CeD-GSRS), and the Physician Global Assessment (PGA). Additional endpoints for NCGS include an ad-hoc list of symptoms (Di Sabatino et al., Clinical Gastroenterology and Hepatology 2015; 13:1604-1612) or a severity patient-reported outcome like a visual analogue scale (VAS) (Elli et al., Nutrients 2016, 8, 84; doi:10.3390/nu8020084).

One of ordinary skill in the art would be able to determine such therapeutically effective amounts based on additional factors as the subject's size, the severity of the subject's symptoms, and the particular composition or route of administration selected.

In some embodiments, the amount or unit dose of the pharmaceutical compositions disclosed herein can include about 50-1000 mg of the anti-IL-15 antibody (e.g., AMG 714) or antigen-biding fragment thereof. In some embodiments, the unit dose can be: about 50-100 mg, about 100-150 mg, about 150-200 mg, about 200-250 mg, about 250-300 mg, about 300-350 mg, about 350-400 mg, about 400-450 mg, about 450-500 mg, about 500-550 mg, about 550-600 mg, about 600-700 mg, about 700-800 mg, about 800-900 mg or about 900-1000 mg, or higher or lower, or any numerical value therebetween, of the anti-IL-15 antibody (e.g., AMG 714) or antigen-biding fragment thereof disclosed herein.

In some embodiments, the amount or unit dose can be: about 50-60 mg, about 60-70 mg, about 70-80 mg, about 80-90 mg, about 90-100 mg, about 100-110 mg, about 110-120 mg, about 120-130 mg, about 130-140 mg, about 140-150 mg, about 150-160 mg, about 160-170 mg, about 170-180 mg, about 180-190 mg, about 190-200 mg, about 200-210 mg, about 210-220 mg, about 220-230 mg, about 230-240 mg, about 240-250 mg, about 250-260 mg, about 260-270 mg, about 270-280 mg, about 280-290 mg, about 290-300 mg, about 300-310 mg, about 310-320 mg, about 320-330 mg, about 330-340 mg, about 340-350 mg, about 350-360 mg, about 360-370 mg, about 370-380 mg, about 380-390 mg, about 390-400 mg, about 400-410 mg, about 410-420 mg, about 420-430 mg, about 430-440 mg, about 440-450 mg, about 450-460 mg, about 460-470 mg, about 470-480 mg, about 480-490 mg, about 490-500 mg, about 500-510 mg, about 510-520 mg, about 520-530 mg, about 530-540 mg, about 540-550 mg, about 550-560 mg, about 560-570 mg, about 570-580 mg, about 580-590 mg, about 590-600 mg, about 600-610 mg, about 610-620 mg, about 630-640 mg, about 640-650 mg, about 650-660 mg, about 660-670 mg, about 670-680 mg, about 680-690 mg, or 690-700 mg, of the anti-IL-15 antibody (e.g., AMG 714) or antigen-biding fragment thereof disclosed herein.

In some embodiments, the amount or unit dose can be: about 50, about 55, about 60, about 65, about 70, about 75, about 80, about 85, about 90, about 95, about 100, about 105, about 110, about 115, about 120, about 125, about 130, about 135, about 140, about 145, about 150, about 155, about 160, about 165, about 170, about 175, about 180, about 185, about 190, about 195, about 200, about 205, about 210, about 220, about 225, about 230, about 235, about 240, about 245, about 250, about 255, about 260, about 265, about 270, about 275, about 280, about 285, about 290, about 295, about 300, about 305, about 310, about 315, about 320, about 325, about 330, about 335, about 340, about 345, about 350, about 355, about 360, about 365, about 370, about 375, about 380, about 385, about 390, about 395, about 400, about 405, about 410, about 415, about 420, about 425, about 430, about 435, about 440, about 445, about 450, about 455, about 460, about 465, about 470, about 475, about 480, about 485, about 490, about 495, about 500, about 505, about 510, about 515, about 520, about 525, about 530, about 535, about 540, about 545, about 550, about 555, about 560, about 565, about 570, about 575, about 580, about 585, about 590, about 595, about 600, about 605, about 610, about 615, about 620, about 625, about 630, about 635, about 640, about 645, about 650, about 655, about 660, about 665, about 670, about 675, about 680, about 685, about 690, about 695, or about 700 mg, or any numerical value in between any two of the foregoing, of the anti-IL-15 antibody (e.g., AMG 714) or antigen-biding fragment thereof disclosed herein.

In some embodiments, the amount or unit dose of the pharmaceutical compositions disclosed herein can include about 1-50 mg/kg (patient weight) of the anti-IL-15 antibody (e.g., AMG 714) or antigen-biding fragment thereof. In some embodiments, the unit dose can be: about 1-10 mg/kg, about 10-20 mg/kg, about 20-30 mg/kg, about 30-40 mg/kg, or about 40-50 mg/kg, or higher or lower, or any numerical value therebetween, of the anti-IL-15 antibody (e.g., AMG 714) or antigen-biding fragment thereof disclosed herein.

In some embodiments, the amount or unit dose can be: about 1-5 mg/kg, about 5-10 mg/kg, about 10-15 mg/kg, about 15-20 mg/kg, about 20-25 mg/kg, about 25-30 mg/kg, about 30-35 mg/kg, about 35-40 mg/kg, about 40-45 mg/kg, or about 45-50 mg/kg. In some embodiments, a preferred dosage can include: about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, or about 50 mg/kg, of the anti-IL-15 antibody (e.g., AMG 714) or antigen-biding fragment thereof disclosed herein.

In some embodiments, each subject can receive at least one (e.g., 1-100) unit dose disclosed herein, depending on the severity of the disease and/or effectiveness of the treatment. For example, the subject may receive 2-20 unit doses which can be the same or different (e.g., one or more initial unit doses can be smaller or larger than later unit dose(s)) from one another.

In some embodiments, the pharmaceutical compositions disclosed herein can be administered, in unit doses disclosed herein, by subcutaneous or intravenous injection every 1-20 weeks. In one embodiment, the pharmaceutical composition is administered subcutaneously. In another embodiment, the pharmaceutical composition is administered intravenously. In certain embodiments, administration can occur every 1-5, 5-10, 10-15, or 15-20 weeks. In some embodiments, administration can occur every 1-2, 2-4, 4-6, 6-8, 8-10, 10-12, 12-14, 14-16, 16-18, or 18-20 weeks. In some embodiments, administration can occur every 1, 2, 3, 4, 5, 6, 7, 8, 9, 10, 11, 12, 13, 14, 15, 16, 17, 18, 19, or 20 weeks. The unit doses can be given at the same intervals (e.g., every 1-20 weeks). Alternatively, at least a portion of the unit doses are given at different (e.g., shortened or prolonged) intervals than the other unit doses.

In other aspects, the present invention relates to a pharmaceutical composition, as described herein, for use in treating celiac or non-celiac gluten sensitivity, wherein the pharmaceutical composition comprises an anti-IL-15 antibody (e.g., AMG 714). In other embodiments, the pharmaceutical composition comprises 75 mg, 150 mg, 300 mg, 450 mg, 600 mg, 4 mg/kg, 8 mg/kg or 12 mg/kg of an anti-IL-15 antibody (e.g., AMG 714). In certain embodiments, the pharmaceutical composition comprises 150 mg or 300 mg of an anti-IL-15 antibody (e.g., AMG 714). In some embodiments, the pharmaceutical composition is administered subcutaneously every 1, 2 or 4 weeks, until, e.g., alleviation or elimination of signs and/or symptoms. In one embodiment, the pharmaceutical composition is administered subcutaneously every 2 weeks. In another particular embodiment, the pharmaceutical composition is administered intravenously every 1, 2 or 4 weeks until, e.g., alleviation or elimination of signs and/or symptoms. In another particular embodiment, the pharmaceutical composition is administered intravenously every 2 weeks.

In some aspects, the present invention relates to a pharmaceutical composition, as described herein, for use in a method of treating celiac or non-celiac gluten sensitivity, wherein the method comprises administering (e.g., subcutaneously) an anti-IL-15 antibody (e.g., AMG 714). In some embodiments, the method comprises administering (e.g., subcutaneously) 75 mg, 150 mg, 300 mg, 450 mg, 600 mg, 4 mg/kg, 8 mg/kg or 12 mg/kg of an anti-IL-15 antibody (e.g., AMG 714). In certain embodiments, the method comprises administering (e.g., subcutaneously) 150 mg or 300 mg of an anti-IL-15 antibody (e.g., AMG 714). In some embodiments, the method comprises administering the pharmaceutical composition subcutaneously every 1, 2 or 4 weeks, until, e.g., alleviation or elimination of signs and/or symptoms. In one embodiment, the method comprises administering subcutaneously every 2 weeks. In another particular embodiment, the method comprises administering intravenously every 1, 2 or 4 weeks until, e.g., alleviation or elimination of signs and/or symptoms. In another particular embodiment, the method comprises administering intravenously every 2 weeks.

In another aspect, the present invention relates to a method of treating celiac or non-celiac gluten sensitivity, wherein the method comprises administering (e.g., subcutaneously) an anti-IL-15 antibody (e.g., AMG 714). In some embodiments, the method comprises administering (e.g., subcutaneously) 75 mg, 150 mg, 300 mg, 450 mg, 600 mg, 4 mg/kg, 8 mg/kg or 12 mg/kg of an anti-IL-15 antibody (e.g., AMG 714). In certain embodiments, the method comprises administering (e.g., subcutaneously) 150 mg or 300 mg of an anti-IL-15 antibody (e.g., AMG 714). In some embodiments, the method comprises administering the pharmaceutical composition subcutaneously every 1, 2 or 4 weeks, until, e.g., alleviation or elimination of signs and/or symptoms. In one embodiment, the method comprises administering subcutaneously every 2 weeks. In another particular embodiment, the method comprises administering intravenously every 1, 2 or 4 weeks until, e.g., alleviation or elimination of signs and/or symptoms. In another particular embodiment, the method comprises administering intravenously every 2 weeks.

In particular embodiments of the pharmaceutical compositions and methods described herein, 150 or 300 or 450 mg of an anti-IL 15 antibody (e.g., AMG 714) is administered once every 2 weeks (q2w) via subcutaneous injection. In another embodiment, the dosing can be 450 mg once every 4 weeks (q4w).

Use of the Pharmaceutical Composition to Treat Refractory Celiac Disease

A rare but specific complication of persistent exposure to gluten in celiac disease is the development of refractory celiac disease (RCD), which affects approximately 1% of celiac patients (Lebwohl et al., 2013). RCD is characterized by severe intestinal mucosal atrophy and gastrointestinal symptoms in the absence of gluten consumption and in the presence of small bowel aberrant IELs (Verbeek et al., 2008, vanWanrooij et al., 2014).

Figure 3:
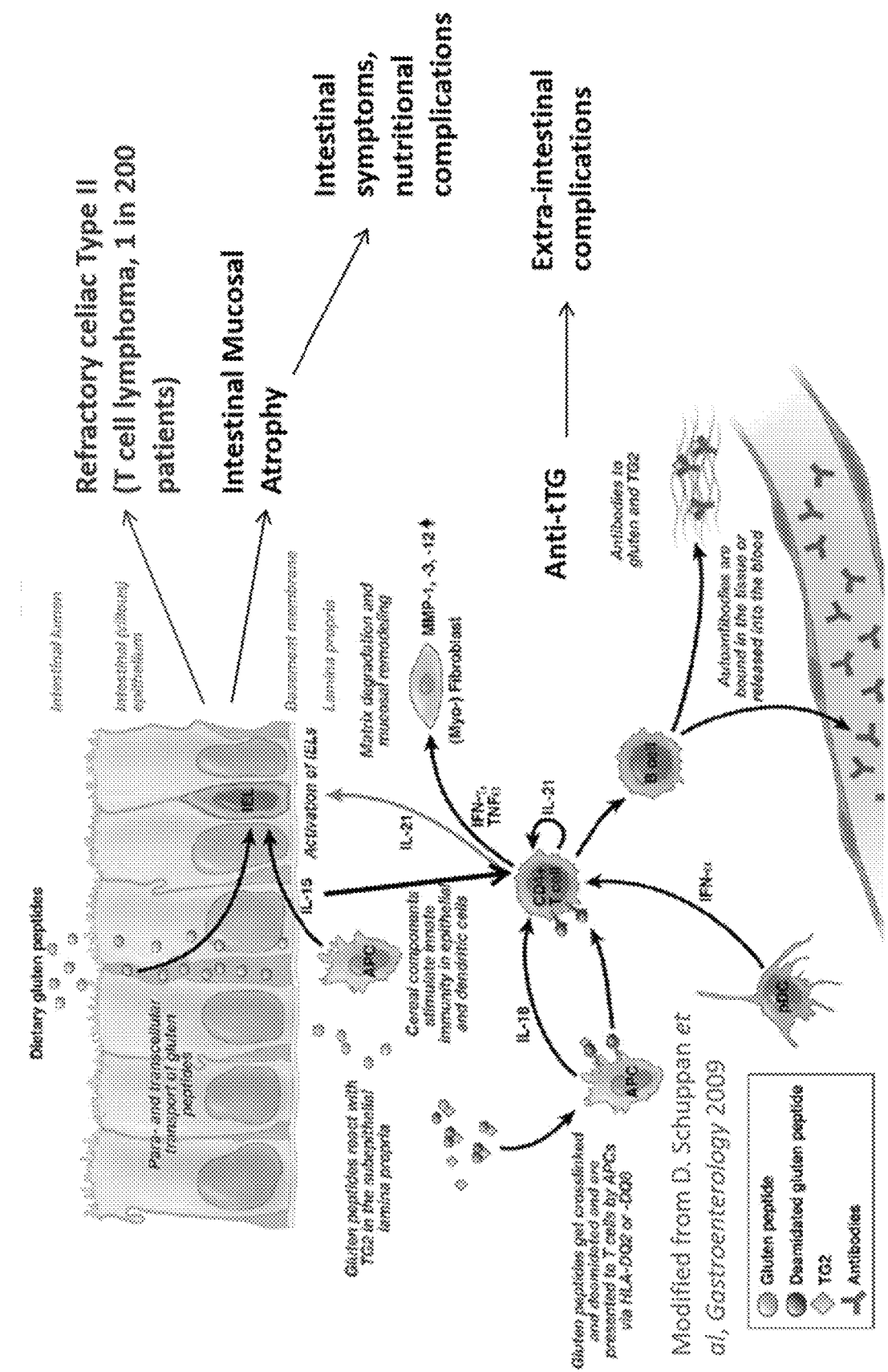
FIG. 3 illustrates a simplified schematic of celiac and refractory celiac disease pathophysiology.

RCD patients can be further classified according to the proportion and characteristics of aberrant IELs. Patients with a low proportion of aberrant IELs, defined as less than 20% of total IELs (less than 20 IELs per 100 epithelial cells), as determined by flow cytometry, are referred to as Type I RCD (RCD-I). These aberrant IELs are generally polyclonal, and RCD-I patients are not at increased risk of developing overt extra epithelial lymphoma (i.e., enteropathy-associated T cell lymphoma [EATL]) and have a typical 5-year survival (vanWanrooij et al., 2014). To treat RCD-I, corticosteroids (local or systemic), azathioprine, purinethol, anti-TNF agents, or cladribine may be used (Brar et al., 2007; Goerres et al., 2003) with clinical and histological improvement. FIG. 3 illustrates the pathophysiology of celiac and refractory celiac disease, as described by Schuppan et al.

Figure 4:
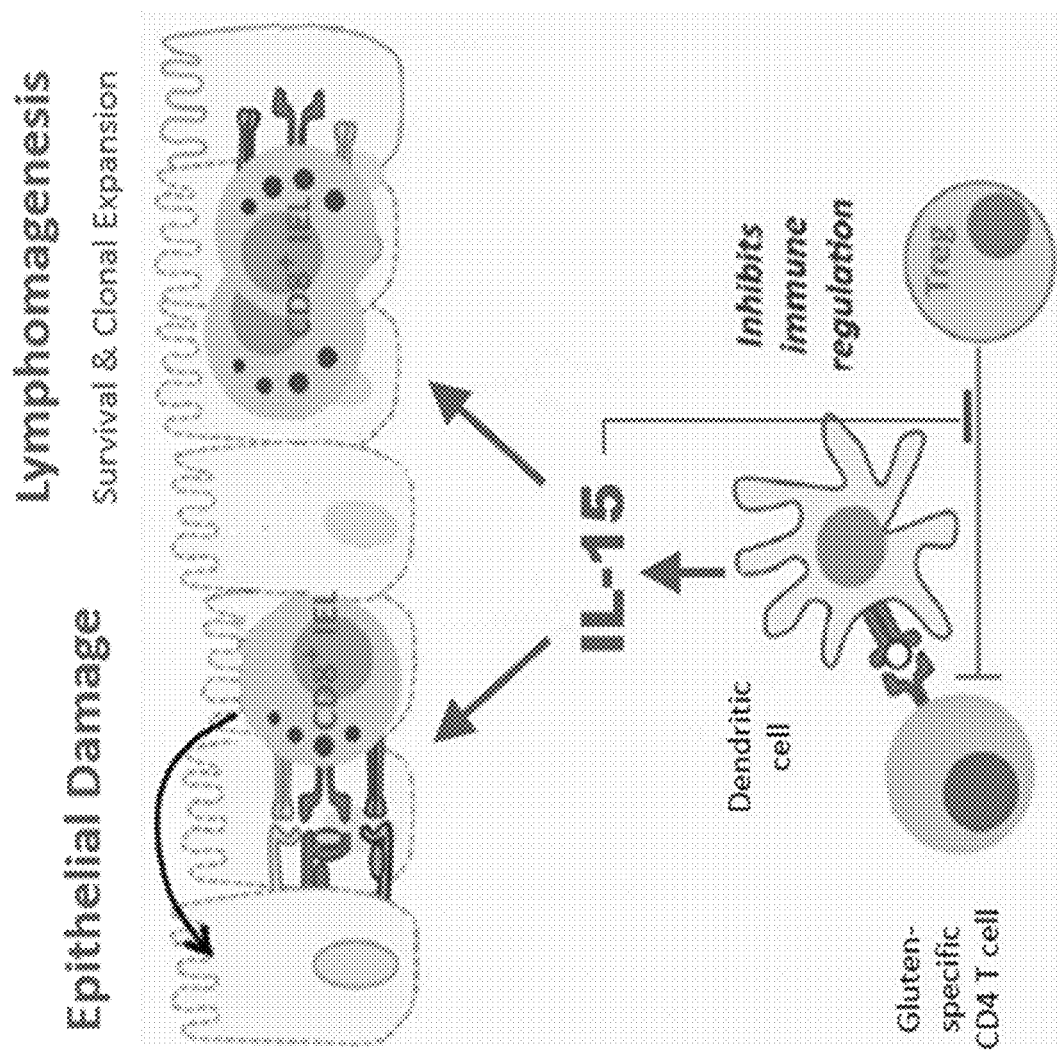
FIG. 4 illustrates a simplified schematic of IL-15 signaling in RCD-II.

When the proportion of aberrant IELs reaches or exceeds 20%, patients are diagnosed with Type II RCD (RCD-II). In RCD-II, the IELs are typically monoclonal and the risk of developing EATL is dramatically increased to greater than 50% (Nijeboer et al., 2015). The aberrant IELs proliferate in the absence of gluten due to accumulation of anti-apoptotic mechanisms, hence the term "refractory" indicating that the disease, a non-Hodgkin slow-growing intraepithelial lymphoma, appears not to be dependent on gluten since it is not responsive to the strictest GFD. As illustrated in FIG. 4, IL-15 is believed to be the main driver of transformation and maintenance of the aberrant IELs (Meresse et al., 2012). Experimental proof of principle has been established for IL-15 inhibition in RCD-II by the finding that blocking IL-15 with the anti-IL-15 mAb AMG 714 induces IEL apoptosis in human small bowel biopsies from active celiac and RCD-II patients (Malamut et al., 2010). Also, IEL apoptosis has been observed in animal models of celiac disease treated with anti-IL-15 AMG 714 (Malamut et al., 2010) or anti-IL-15-receptor mAbs (Yokoyama et al., 2009).

The aberrant monoclonal IELs have been demonstrated to be precursors of EATL based on the observation that the T cell receptor (TCR) re-arrangement repertoire is similar in sequential biopsies from RCD-II patients who develop EATL. RCD-II is considered to be an in situ low-grade T cell lymphoma of the small bowel. A thorough study of the low grade IEL proliferation in RCD-II has revealed a characteristic phenotype with the presence of intracellular CD3 without surface CD3 or TCR and generally no CD8 expression with expression of CD103, which is shared by high grade EATL proliferations. This phenotype is distinct from the normal phenotype of IELs in uncomplicated celiac disease and, together with the common presence of a clonal TCR re-arrangement in the intestinal biopsy, confirms the diagnosis of RCD and allows follow-up of the expansion.

The treatment of RCD-II is difficult as aberrant lymphocytes are scattered throughout the whole small intestinal epithelium and, usually, in the stomach and colon, thereby precluding surgery. In addition, there is no standard of care for RCD-II. Attempts of chemotherapies have been mostly ineffective and/or dangerous for patients. Cladribine (Tack et al., 2011a; Tack et al., 2011b) and autologous bone marrow transplantation have been used and shown to transiently improve the digestive symptoms and histology but not monoclonal proliferation. The prognosis of RCD-II is poor, with death occurring within 3-10 years mainly due to intractable diarrhea, EATL, or the rare dissemination of low grade lymphocyte proliferation to other tissues (e.g., skin, lungs).

EATL is a high-grade, systemic, T cell lymphoma almost exclusively seen as a complication of RCD-II (Nijeboer et al., 2015). Diagnosis includes imaging and histology to demonstrate the presence of malignant T cells in extra-epithelial locations such as lymph nodes or other organs. The treatment of EATL relies on surgical resection and chemotherapy, but the prognosis is very poor, with a 5-year survival of less than 20% (Nijeboer et al., 2015).

The incidence of EATL is increasing, and this increase could be related to the rising prevalence of gluten contamination in the diet over prolonged periods of time (Sharaiha et al., 2012). An effective treatment for RCD-II that could alleviate the presence of aberrant IELs, the histological abnormalities, and/or the symptoms remains the highest priority. A summary of the characteristics of CD, RCD, and ETCL are summarized in Table 1 below.

TABLE 1

Characteristics of Celiac Disease, Refractory Celiac Disease, and Enteropathy-associated T cell Lymphoma

| Type | Nature of the disease | Gluten dependence | Aberrant IELs | Clonality | Progression to overt systemic lymphoma |
|---|---|---|---|---|---|
| Non-Responsive Celiac Disease | Autoimmune | Yes | No | Polyclonal | No |
| Refractory Type I | Unknown | Probably | Yes, less than 20% | Oligoclonal | No |
| Refractory Type II | Malignant, slow growing | Probably independent | Yes, greater than 20% | Monoclonal (in situ lymphoma) | greater than 50% |
| EATL | Malignant, rapid progression | No | Yes, greater than 20% | Monoclonal (systemic lymphoma) | N/A |

The present invention provides methods and compositions for treating Type I or Type II Refractory Celiac Disease by administering a therapeutically effective amount of an anti-IL-15 antibody (e.g., AMG 714) or antigen-binding fragment thereof disclosed herein. In some embodiments, a therapeutically effective amount of the anti-IL-15 antibody (e.g., AMG 714) or antigen-binding fragment thereof can achieve, e.g., for the treatment of RCD-I or RCD-II one or more of, (1) a measure of the immunological response by quantification of the reduction from baseline in the % of aberrant intestinal intraepithelial lymphocytes (IELs) vs. total IELs as assessed by flow-cytometry, (2) the measure of the immunological response by quantification of the reduction from baseline in the % of aberrant IELs vs. intestinal epithelial cells, (3) histological response: Improvement from baseline in small intestinal villous height to crypt depth (VH:CD) ratio, Marsh score or total IEL counts, and/or (4) clinical response: Change from baseline in clinical symptoms by the Bristol Stool Form Scale (BSFS), the Celiac Disease Patient-Reported Endpoint (CeD PRO), and Gastrointestinal Symptom Rating Scale (GSRS), including the celiac disease GSRS (CeD-GSRS).

In some embodiments, the amount or unit dose of the pharmaceutical compositions disclosed herein can include about 1-50 mg/kg (patient weight) of the anti-IL-15 antibody (e.g., AMG 714) or antigen-biding fragment thereof. In some embodiments, the unit dose can be: about 1-10 mg/kg, about 10-20 mg/kg, about 20-30 mg/kg, about 30-40 mg/kg, or about 40-50 mg/kg, or higher or lower, or any numerical value therebetween, of the anti-IL-15 antibody (e.g., AMG 714) or antigen-biding fragment thereof disclosed herein.

In some embodiments, the amount or unit dose can be: about 1-5 mg/kg, about 5-10 mg/kg, about 10-15 mg/kg, about 15-20 mg/kg, about 20-25 mg/kg, about 25-30 mg/kg, about 30-35 mg/kg, about 35-40 mg/kg, about 40-45 mg/kg, or about 45-50 mg/kg. In some embodiments, a preferred dosage can include: about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, or about 50 mg/kg, of the anti-IL-15 antibody (e.g., AMG 714) or antigen-biding fragment thereof disclosed herein.

In some embodiments, the amount or unit dose of the pharmaceutical compositions disclosed herein can include about 50-1000 mg of the anti-IL-15 antibody (e.g., AMG 714) or antigen-biding fragment thereof. In some embodiments, the unit dose can be: about 50-100 mg, about 100-150 mg, about 150-200 mg, about 200-250 mg, about 250-300 mg, about 300-350 mg, about 350-400 mg, about 400-450 mg, about 450-500 mg, about 500-550 mg, about 550-600 mg, about 600-700 mg, about 700-800 mg, about 800-900 mg or about 900-1000 mg, or higher or lower, or any numerical value therebetween, of the anti-IL-15 antibody (e.g., AMG 714) or antigen-biding fragment thereof disclosed herein.

In some embodiments, the amount or unit dose can be: about 50-60 mg, about 60-70 mg, about 70-80 mg, about 80-90 mg, about 90-100 mg, about 100-110 mg, about 110-120 mg, about 120-130 mg, about 130-140 mg, about 140-150 mg, about 150-160 mg, about 160-170 mg, about 170-180 mg, about 180-190 mg, about 190-200 mg, about 200-210 mg, about 210-220 mg, about 220-230 mg, about 230-240 mg, about 240-250 mg, about 250-260 mg, about 260-270 mg, about 270-280 mg, about 280-290 mg, about 290-300 mg, about 300-310 mg, about 310-320 mg, about 320-330 mg, about 330-340 mg, about 340-350 mg, about 350-360 mg, about 360-370 mg, about 370-380 mg, about 380-390 mg, about 390-400 mg, about 400-410 mg, about 410-420 mg, about 420-430 mg, about 430-440 mg, about 440-450 mg, about 450-460 mg, about 460-470 mg, about 470-480 mg, about 480-490 mg, about 490-500 mg, about 500-510 mg, about 510-520 mg, about 520-530 mg, about 530-540 mg, about 540-550 mg, about 550-560 mg, about 560-570 mg, about 570-580 mg, about 580-590 mg, about 590-600 mg, about 600-610 mg, about 610-620 mg, about 630-640 mg, about 640-650 mg, about 650-660 mg, about 660-670 mg, about 670-680 mg, about 680-690 mg, or 690-700 mg, of the anti-IL-15 antibody (e.g., AMG 714) or antigen-biding fragment thereof disclosed herein.

In some embodiments, the amount or unit dose can be: about 50, about 55, about 60, about 65, about 70, about 75, about 80, about 85, about 90, about 95, about 100, about 105, about 110, about 115, about 120, about 125, about 130, about 135, about 140, about 145, about 150, about 155, about 160, about 165, about 170, about 175, about 180, about 185, about 190, about 195, about 200, about 205, about 210, about 220, about 225, about 230, about 235, about 240, about 245, about 250, about 255, about 260, about 265, about 270, about 275, about 280, about 285, about 290, about 295, about 300, about 305, about 310, about 315, about 320, about 325, about 330, about 335, about 340, about 345, about 350, about 355, about 360, about 365, about 370, about 375, about 380, about 385, about 390, about 395, about 400, about 405, about 410, about 415, about 420, about 425, about 430, about 435, about 440, about 445, about 450, about 455, about 460, about 465, about 470, about 475, about 480, about 485, about 490, about 495, about 500, about 505, about 510, about 515, about 520, about 525, about 530, about 535, about 540, about 545, about 550, about 555, about 560, about 565, about 570, about 575, about 580, about 585, about 590, about 595, about 600, about 605, about 610, about 615, about 620, about 625, about 630, about 635, about 640, about 645, about 650, about 655, about 660, about 665, about 670, about 675, about 680, about 685, about 690, about 695, or about 700 mg, or any numerical value in between any two of the foregoing, of the anti-IL-15 antibody (e.g., AMG 714) or antigen-biding fragment thereof disclosed herein.

In some embodiments, each subject can receive at least one (e.g., 1-100) unit dose disclosed herein, depending on the severity of the disease and/or effectiveness of the treatment. For example, the subject may receive 2-20 unit doses which can be the same or different (e.g., one or more initial unit doses can be smaller or larger than later unit dose(s)) from one another.

In some embodiments, the pharmaceutical compositions disclosed herein can be administered, in unit doses disclosed herein, by subcutaneous or intravenous injection every 1-20 weeks. In one embodiment, the pharmaceutical composition is administered subcutaneously. In another embodiment, the pharmaceutical composition is administered intravenously. In certain embodiments, administration can occur every 1-5, 5-10, 10-15, or 15-20 weeks. In some embodiments, administration can occur every 1-2, 2-4, 4-6, 6-8, 8-10, 10-12, 12-14, 14-16, 16-18, or 18-20 weeks. In some embodiments, administration can occur every 1, 2, 3, 4, 5, 6, 7, 8, 9, 10, 11, 12, 13, 14, 15, 16, 17, 18, 19, or 20 weeks. The unit doses can be given at the same intervals (e.g., every 1-20 weeks). Alternatively, at least a portion of the unit doses are given at different (e.g., shortened or prolonged) intervals than the other unit doses. In one example, one or more additional loading doses can be given at, e.g., week 1 or any other time to boost the dosage.

In other aspects, the present invention relates to a pharmaceutical composition, as described herein, for use in treating Type II refractory celiac disease patients, e.g., patients with in situ small bowel T Cell lymphoma, wherein the pharmaceutical composition comprises an anti-IL-15 antibody (e.g., AMG 714). In other embodiments, the pharmaceutical composition comprises 75 mg, 150 mg, 300 mg, 600 mg, 4 mg/kg, 8 mg/kg or 12 mg/kg of an anti-IL-15 antibody (e.g., AMG 714). In a particular embodiment, the pharmaceutical composition comprises 8 mg/kg of AMG 714. In some embodiments, the pharmaceutical composition is administered (e.g., intravenously) every 1, 2 or 4 weeks, until, e.g., alleviation or elimination of signs and/or symptoms. In another particular embodiment, pharmaceutical composition is administered (e.g., intravenously) every 2 weeks. In another particular embodiment, the pharmaceutical composition is administered subcutaneously every 1, 2 or 4 weeks until, e.g., alleviation or elimination of signs and/or symptoms. In another particular embodiment, the pharmaceutical composition is administered subcutaneously every 2 weeks.

In some aspects, the present invention relates to a pharmaceutical composition, as described herein, for use in a method of treating Type II refractory celiac disease patients e.g., patients with in situ small bowel T Cell lymphoma, wherein the method comprises administering (e.g., intravenously) an anti-IL-15 antibody (e.g., AMG 714). In some embodiments, the method comprises administering (e.g., intravenously) 75 mg, 150 mg, 300 mg, 450 mg, 600 mg, 4 mg/kg, 8 mg/kg or 12 mg/kg of an anti-IL-15 antibody (e.g., AMG 714). In certain embodiments, the method comprises administering (e.g., intravenously) 8 mg/kg of an anti-IL-15 antibody (e.g., AMG 714). In some embodiments, the method comprises administering the pharmaceutical composition subcutaneously every 1, 2 or 4 weeks, until, e.g., alleviation or elimination of signs and/or symptoms. In one embodiment, the method comprises administering subcutaneously every 2 weeks. In another particular embodiment, the method comprises administering intravenously every 1, 2 or 4 weeks until, e.g., alleviation or elimination of signs and/or symptoms. In another particular embodiment, the method comprises administering intravenously every 2 weeks.

In another aspect, the present invention relates to a method of treating Type II refractory celiac disease patients or patients with in situ small bowel T Cell lymphoma, wherein the method comprises administering (e.g., intravenously) an anti-IL-15 antibody (e.g., AMG 714). In some embodiments, the method comprises administering (e.g., intravenously) 75 mg, 150 mg, 300 mg, 450 mg, 600 mg, 4 mg/kg, 8 mg/kg or 12 mg/kg of an anti-IL-15 antibody (e.g., AMG 714). In certain embodiments, the method comprises administering (e.g., intravenously) 8 mg/kg of an anti-IL-15 antibody (e.g., AMG 714). In some embodiments, the method comprises administering the pharmaceutical composition subcutaneously every 1, 2 or 4 weeks, until, e.g., alleviation or elimination of signs and/or symptoms. In one embodiment, the method comprises administering subcutaneously every 2 weeks. In another particular embodiment, the method comprises administering intravenously every 1, 2 or 4 weeks until, e.g., alleviation or elimination of signs and/or symptoms. In another particular embodiment, the method comprises administering intravenously every 2 weeks.

In particular embodiments of the pharmaceutical compositions and methods described herein, 8 mg/kg of an anti-IL-15 antibody (e.g., AMG 714) is administered once every 2 weeks (q2w) intravenously. In other particular embodiments of the pharmaceutical compositions and methods described herein, 8 mg/kg of an anti-IL 15 antibody (e.g., AMG 714) is administered intravenously at week 0, week 1, and once every 2 weeks (q2w) thereafter. In another embodiment, the dosing can be 450 mg once every 4 weeks (q4w).

EXAMPLES

Example 1: Phase 2a, Randomized, Double-Blind, Placebo-Controlled, Parallel-Group Study to Evaluate Efficacy and Safety of AMG 714 in Adult Patients with Celiac Disease

SUMMARY

In an exemplary clinical trial, AMG 714 was administered to adult patients with CD. The objective of this trial was to determine the potential therapeutic benefits of AMG 714, an investigational anti-IL-15 monoclonal antibody, in patients with gluten-free diet (GFD) non-responsive celiac disease (NRCD), by investigating the drug's ability to attenuate the effects of gluten exposure in adults with celiac disease.

In particular, the study was designed to:

Assess the effect of study drug (AMG 714 or placebo) on the attenuation of mucosal abnormalities and symptoms in subjects with well-controlled celiac disease, who were receiving a 10-week high-dose daily gluten challenge (GC); hereafter referred to as "Per Protocol Population 1" (PP1). This investigation evaluated the potential indication of AMG 714 as a (partial) Replacement for GFD.

Obtain an initial understanding of the effect of AMG 714 in subjects with persistent mucosal abnormality despite adherence to a GFD who received study drug without high-dose daily GC; hereafter referred to as "Per Protocol Population 2" (PP2). This investigation explored the potential indication of AMG 714 as an Adjunct to the GFD.

Assess the dose response of AMG 714 at 150 mg and 300 mg.

While the primary endpoint—protection from reduction in villous height to crypt depth ratio (VH:CD) upon gluten challenge—was not statistically significant in this study, there was a 6.4% difference (equivalent to a 11% reduction) in the 300 mg AMG 714 group compared to placebo. The totality of the PP1 efficacy results (approximately 15 subjects per group), including statistical significance in attenuation of increased intraepithelial lymphocytes (IELs) and clinical symptoms (CeD-PRO, BSFS Diarrhea) between the 300 mg q2w dose of AMG 714 and placebo, and efficacy signals in most other secondary and exploratory endpoints (CeD-GSRS, anti-DGP serology, Physician Global Assessment), indicates that AMG 714 can attenuate the effects of a substantial dose (2 to 4 g) of daily GC. Thus, the proof of concept (POC) for AMG 714 in celiac disease has been established.

Over a 12-week study period, AMG 714 300 mg reduced the impact of high-dose daily GC on inflammation (38% lower increase in IEL, p=0.03) and symptoms, as measured by the Celiac Disease Patient-Reported Outcome (CeD-PRO) score (p=0.02), the Celiac Disease Gastrointestinal Symptom Rating Scale (CeD-GSRS) score (p=0.07), Weeks with Diarrhea according to the Bristol Stool Form Scale (BSFS) (p=0.0002), and the Physician Global Assessment (PGA, p=0.01); as compared with placebo. Most other pre-specified outcomes also showed consistent directionality in favor of the 300 mg arm compared with placebo: anti-DGP IgA and IgG; and reduction of serum IL-15. AMG 714 did not alter the production of anti-tTG IgA triggered by daily GC, thus clinically confirming previous observations in a mouse model of IL-15-driven celiac disease. Further, results suggest a dose-dependent effect on efficacy endpoints, with the 300 mg dose showing greater attenuation of the effects of gluten challenge than the 150 mg dose across most endpoints, albeit not reaching statistical significance in all cases.

The efficacy results for the PP1 population are summarized Table 2:

TABLE 2

| Attenuation of effects of high-dose gluten challenge (PP1) | 150 mg AMG 714 versus Placebo | | 300 mg AMG 714 versus Placebo | |
|---|---|---|---|---|
| | Attenuation | LS Mean Difference | Attenuation | LS Mean Difference |
| VH:CD change from baseline | No attenuation | −2.50 p = 0.73 | 10.59% | 6.39 p = 0.35 |
| IEL change from baseline | 13.1% | −14.32 p = 0.47 | 37.6% | −41.24 p = 0.03 |
| CeD PRO (AUC) | 21% | −0.17 p = 0.24 | 38% | −0.31 p = 0.02 |
| CeD-GSRS (AUC) | 68% | −2.01 p = 0.18 | 84% | −2.51 p = 0.07 |
| Weeks with Diarrhea (BSFS ≥6) | 100% | −12.46 p = 0.01 | 100% | −18.00 p = 0.0002 |
| Clinically Active Disease (PGA >2) at Week 12 | 60% | −0.20 p = 0.39 | 100% | −0.33 p = 0.01 |

Abbreviations:
AUC = area under the curve,
BSFS = Bristol Stool Form Scale,
CeD-GSRS = Celiac Disease Gastrointestinal Symptom Rating Scale,
CcD PRO = celiac disease patient-reported outcome,
IEL = intraepithelial lymphocyte,
LS = least square,
PGA = Physician Global Assessment,
PP = per-protocol population,
VH:CD = villous height-to-crypt depth ratio.
Note:
Attenuation is defined as the difference between active treatment and placebo, normalized to placebo; i.e., LS mean difference divided by placebo value, capped at 100% if AMG 714 fully prevented the effect of gluten on a certain endpoint.

Efficacy results in PP2 (no daily GC), while not statistically significant due in part to the small sample size (2-5 subjects per group), showed numerical benefits in subjects on AMG 714 across most endpoints.

The totality of the PP1 efficacy results in all efficacy endpoints (approximately 15 subjects per group) indicate that AMG 714 300 mg bi-weekly can reduce the effects of a substantial dose of daily gluten (2 to 4 g per day), as statistical significance was achieved between AMG 714 300 mg and placebo in:
  reduction of increased IELs (41% difference compared to placebo, a 38% attenuation of the effect of gluten challenge),
  improvement of clinical symptoms: CeD-PRO, BSFS Diarrhea
  PGA at Week 12

In addition, efficacy signals in anti-DGP serology and serum IL-15 were noted. Thus, the proof of mechanism for IL-15 inhibition and the proof of concept for AMG 714 treatment in celiac disease has been established. Further, the results suggest a dose-dependent effect, as the 300 mg dose was directionally more efficacious than the 150 mg dose across most endpoints, though not statistically different. This suggests that a higher dose may have reached greater effect sizes. This is consistent with the lack of full suppression of serum IL-15 in all treatment groups except 300 mg AMG 714 in PP2. It is possible that a higher dose of AMG 714 in PP1 could have resulted in greater inhibition of serum IL-15 and led to greater efficacy. Efficacy results in PP2 (no daily gluten challenge), while mostly not statistically significant due to the small sample size (2-5 subjects per group), showed numerical benefits in subjects on AMG 714 in most endpoints, including VH:CD, IELs, and CeD-PRO.

Pharmacokinetic (PK) analysis showed twice the amount of drug exposure as was observed in a previous Phase 2a psoriasis study (ClinicalTrials.gov Identifier: NCT00443326), probably due to lower body weight and predominantly female subjects in this study. Up to 14% of patients developed anti-drug antibodies (ADA), but all ADAs were non-neutralizing, had no impact on PK, and were not associated with any AEs, except mild injection site reaction. This result should be viewed with caution, as pre-existing ADAs were reported in 10% of patients.

Preliminary analysis of PK/PD correlation indicates an exposure/response association in the 300 mg dose. This suggests that a higher dose may reach greater effect sizes.

The safety and tolerability of AMG 714 was favorable in this study. There were no serious adverse events (SAEs), and the frequencies of adverse events (AEs) were generally similar between each AMG 714 dose group and the placebo group. The proportion of subjects with injection site reactions was slightly greater in the AMG 714 groups than in the placebo group, with a dose-related increase between 150 mg and 300 mg. A majority of these AEs were mild and resolved on treatment. Two of 62 subjects discontinued treatment due to an AE (one on 150 mg and one on 300 mg). Up to 14% of patients developed anti-drug antibodies (ADA), but all ADAs were non-neutralizing, had no impact on PK, and were not associated with any AEs except mild injection site reaction. Pre-existing ADAs were reported in 10% of patients.

Taking all results together, the study demonstrated POC for AMG 714 in the treatment of celiac disease. This is the first study in celiac disease with simultaneous histological (IEL) and clinical benefit. VH:CD benefit appears to lag IEL and clinical improvements in this patient population, which was sicker at baseline (i.e., immunologically primed) and exposed to a larger daily gluten dose than in other similarly conducted trials in patients with celiac disease.

In conclusion, in this first study of AMG 714 in NRCD patients, AMG 714 demonstrated consistent efficacy signals across multiple endpoints (e.g., symptoms, gut inflammatory cells, physician assessment). In addition, AMG 714 at doses up to 300 mg was well tolerated, with no serious or unexpected safety concerns in this patient population. The clear dose-response suggests that increasing dose levels above 300 mg could lead to greater efficacy.

The study establishes IL-15 inhibition as relevant in celiac disease and supports continued exploration of AMG 714 for an indication of adjunctive treatment to the GFD.

In some embodiments, AMG 714 may be beneficial as "an adjunctive treatment to GFD".

The next study, a Phase 2b GFD study, should explore a wider range of doses of AMG 714, including higher doses for greater effect size, and a lower dose to establish the minimally effective dose.

Study Design

The protocol was designed to be a Phase 2a, randomized, double-blind, placebo-controlled, parallel-group study to evaluate the efficacy and safety of AMG 714 for the attenuation of the effects of gluten exposure in adult patients with celiac disease during a gluten challenge. The primary objective of this study was to assess the efficacy of AMG 714 in attenuating the effects of gluten exposure in adults with CD. The secondary objective was to assess the safety and tolerability of AMG 714 when administered to adult patients with celiac disease exposed to a gluten challenge. The exploratory objectives were to assess the pharmacokinetics (PK), pharmacodynamics (PD), and PK/PD correlations of AMG 714.

All subjects were randomized at a 1:1:1 ratio to receive 150 mg or 300 mg AMG 714 or placebo once every two weeks for 10 weeks. Randomization was stratified by site and sex. The study drug (AMG 714 or placebo) was administered at the clinical site in a double-blind fashion via subcutaneous (SC) injection.

In addition to receiving study medication or placebo, all subjects in PPI Population were required to consume either placebo gluten (for the first 2 weeks) and active gluten (2-4 grams per day, during weeks 3 thru 12) administered in a single-blind fashion. Subjects with mucosal atrophy at baseline or very high sensitivity to gluten were exempt from gluten challenge and comprised the PP2 Population.

Subjects' adherence to GFD and consumption of Sponsor-provided gluten were periodically assessed using the iVYLISA gluten immunogenic peptide (GIP) tests on stool and urine samples. Subjects with known or suspected GFD transgressions or suspected noncompliance to study-provided gluten consumption were counseled but allowed to continue in the study.

All study subjects who met all other study entry criteria underwent upper gastrointestinal endoscopy and biopsy prior to baseline (Visit 1, Week 0/Day 0) and at the end of the 12-week study period while still on the gluten challenge and within 5 days before Visit 7 (Week 12/Day 84) in order to assess changes from baseline in VH:CD ratio, IELs, and Marsh score.

All subjects completed the Bristol Stool Form Scale (BSFS) at the time of each bowel movement, from baseline (Visit 1, Week 0/Day 0) through the final study visit (Visit 8, Week 16/Day 112). Subjects completed the Celiac Disease Patient Reported Outcome (CeD PRO) assessment daily, from baseline to the final study visit. Subjects also completed the Gastrointestinal Symptom Rating Scale (GSRS) at screening and weekly from baseline through the study final study visit. The BSFS, GSRS and CeD PRO scores were measured using a handheld electronic diary at times specified in the Schedule of Procedures.

Safety parameters were monitored on an ongoing basis and subjects could undergo unscheduled visits for safety reasons, if needed. Safety assessments included clinical laboratory tests, physical examination, vital signs, and AE monitoring.

A total of 64 patients were enrolled. Subject inclusion criteria:
Diagnosis of celiac disease by intestinal biopsy at least 12 months prior to screening
On a gluten-free diet for at least 12 months
Negative celiac serology
Avoidance of pregnancy
Exclusion criteria:
Severe complications of celiac disease, such as refractory celiac disease
Celiac symptoms
Other concomitant autoimmune disease
Chronic, active GI disease
Infections, concomitant diseases
Prohibited medications The selection of dosing levels for the celiac disease study, in one embodiment, is 150 or 300 or 450 mg once every 2 weeks (q2w) via subcutaneous injection (SC). In another embodiment, the dosing can be 450 mg once every 4 weeks (q4w). While there is no prior experience with AMG 714 in celiac disease nor any understanding of the potential PK/PD relationship in this disease, toxicology and human studies to date support the dosing regimen selected for this study. The highest doses of AMG 714 studied in previous clinical trials were a single SC dose of 700 mg and SC doses of 300 mg every two weeks for 12 weeks, with no safety signals identified to date.

The dosing regimen was expected to provide trough levels above the concentration of AMG 714 used in vitro (10 µg/mL) to induce apoptosis of activated IELs in biopsies of patients with active celiac disease (Malamut et al., 2010).

Serum exposure was monitored with frequent PK sampling. Tissue effects were monitored with experimental biomarkers measured in the biopsies obtained throughout the study.

Criteria for Evaluation:
Efficacy:
Small-bowel biopsies were collected for histological assessments, including the VH:CD ratio, density of CD3-positive IEL, the Marsh-Oberhuber score, mRNA analysis, and optional research assessments.
Anti-tTG auto-antibodies, Anti-deamidated gliadin peptide (DGP) antibodies (anti-DGP, IgA and IgG)
BSFS
GSRS, CeD GSRS
CeD PRO
Safety:
Treatment-emergent AEs, SAES, AE severity, and relationship with study drug
Clinical laboratory
Vital signs
Physical examination
Exploratory:
PK, PD, and PK/PD correlation
iVYLISA GIP tests
Physician Global Assessment (PGA)
Biomarkers of disease activity
Immunogenicity of AMG 714

Analysis Datasets: The populations for analysis were per-protocol (PP) and intent-to-treat (ITT) populations. PP Population is defined as: all randomized subjects and who received at least one dose of the study drug, excluding non-evaluable subjects. Those receiving Gluten Challenge (GC) were analyzed as PP1 and those who did not receive GC (or just for a few days) due to atrophy at baseline and/or high sensitivity to gluten were included in PP2. ITT Population is defined as: all randomized subjects who received at least one dose of the study drug. Subjects were analyzed in the treatment group to which they were randomized. Subjects with only one measurement available were excluded from the ITT population for any endpoints that were defined as change from baseline. Safety population was the same as the ITT population.

Efficacy Analyses: The primary efficacy endpoint was the difference in the percentage of reduction of VH:CD ratio from baseline to Week 12, compared between the two AMG 714 dose groups and the placebo group. The villous height and crypt depth were measured and their ratio (VH:CD ratio) was calculated at each time point. The results of the AMG 714 150 mg and 300 mg dose groups were compared with that of the placebo group separately.

The secondary endpoints included:
IEL: As an indicator of mucosal inflammation, the density of CD3-positive IELs per 100 epithelial cells was calculated.
Marsh-Oberhuber classes, Marsh 0, 1, 2, 3a-c. Grouping by converting the morphometric results into Marsh classes (Maki-Jilab converter).
GSRS and CeD-GSRS scores by week
BSFS score and number of bowel movements by day and week Serology: Anti-tTG IgA and anti-DGP IgA and IgG levels
Exploratory endpoints included: PGA, CeD-PRO, Serum IL-15.

The efficacy endpoints were analyzed using the PP populations.

Safety Analyses: All AEs were coded using MedDRA and summarized by system organ class (SOC) and preferred term (PT), and separately by causality and severity. Other safety variables assessed were: clinical laboratory tests, physical examination, and vital signs. For the assessment of immunogenicity, the number and percent of subjects who developed binding antibodies and those who developed neutralizing antibodies were summarized. All safety variables were summarized by treatment group. Some of the variables were tabulated by treatment group and by visit.

Subject Disposition

Figure 18:
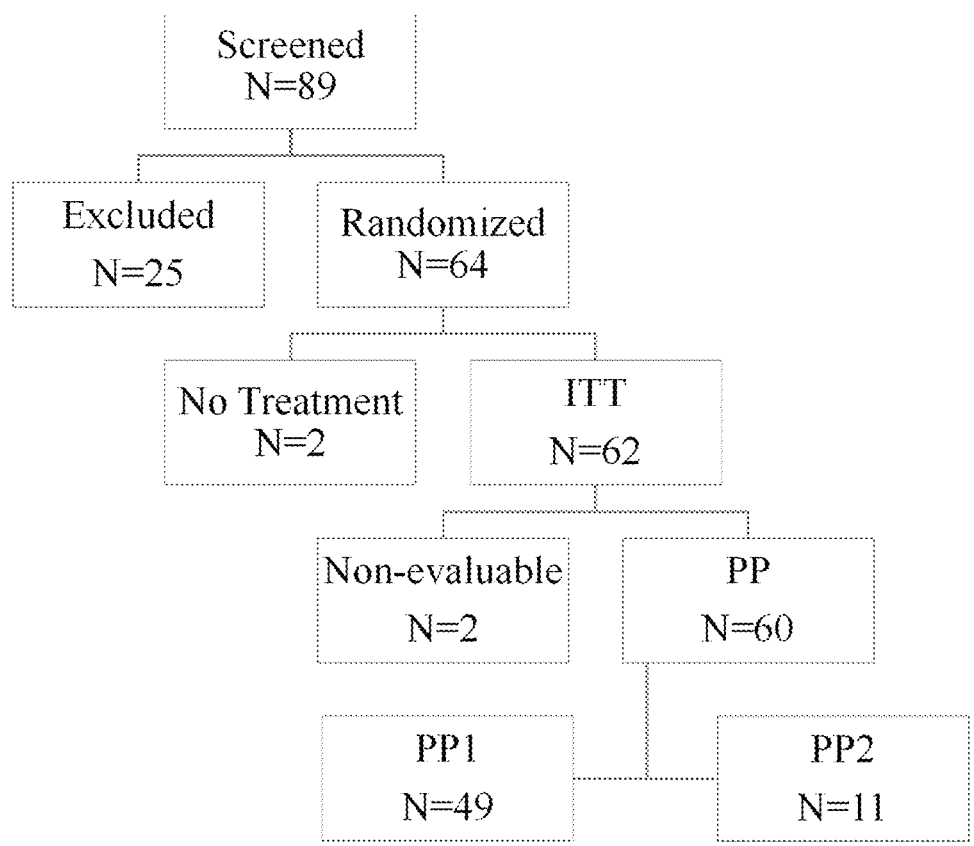
FIG. 18 shows an overview of subject allocation in a Phase 2a, randomized, double-blind, placebo-controlled, parallel-group study to evaluate the efficacy and safety of AMG 714 in adult patients with celiac disease.

An overview of subject allocation is shown in FIG. 18.

PP1 included 49 subjects who underwent gluten challenge. PP2 included 11 subjects who did not undergo gluten challenge or did so only for a few days. The number of subjects in the 3 treatment groups in the PP1 population was well-balanced. PP2 population was comprised of patients with atrophy at baseline, suggesting they were eating some gluten in their GFD, who did not receive GC (n=8); and patients who started GC but received only a few days of challenge due to high acute sensitivity (n=3).

These patients would have been excluded from other GC trials. Thus, PP2 serves as an additional set of data to help gain more insight for further research. The PP2 population was not powered for any of the endpoints in the study, nor stratified. As a result, only 2 of the 11 patients in PP2 received 300 mg AMG 714, which made statistical comparisons with placebo unfeasible.

Of all 62 subjects in the ITT population, 74.2% were female, which is consistent with the general patient population. The mean age was 51.1 years; the median age was 55.0 years (range 19 to 72). All subjects were Caucasian. The mean body mass index (BMI) was 25.7 kg/m$^2$. Overall, the demographic and baseline characteristics were well-balanced across the 3 treatment groups.

Efficacy Results

Primary Efficacy Analysis

The primary efficacy endpoint was the comparison between each AMG 714 dose with placebo in the relative (%) change from baseline to Week 12 in VH:CD ratio.

Figure 6B:
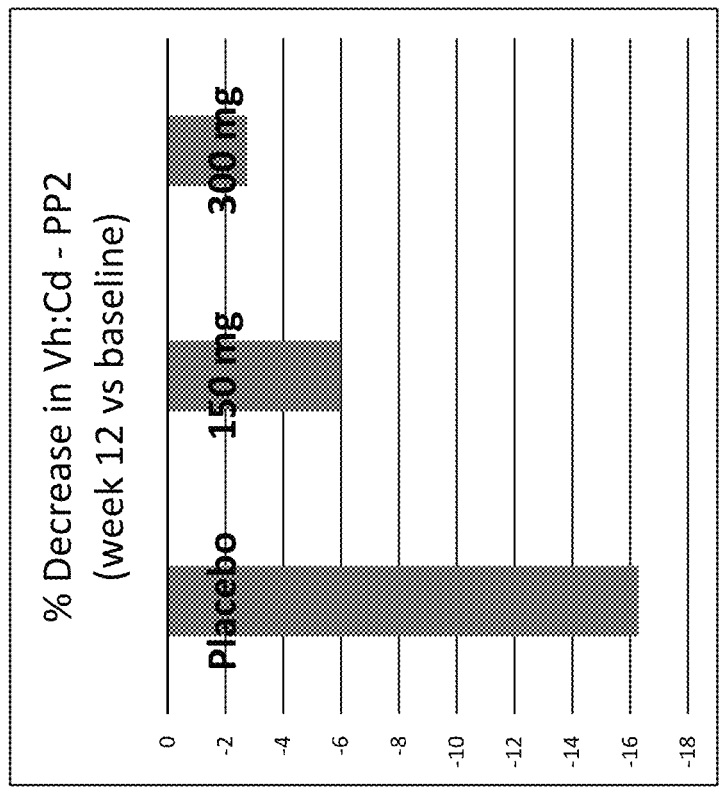
FIG. 6B shows relative (%) decrease from baseline in VH:CD ratio (PP2 Population).
Figure 6A:
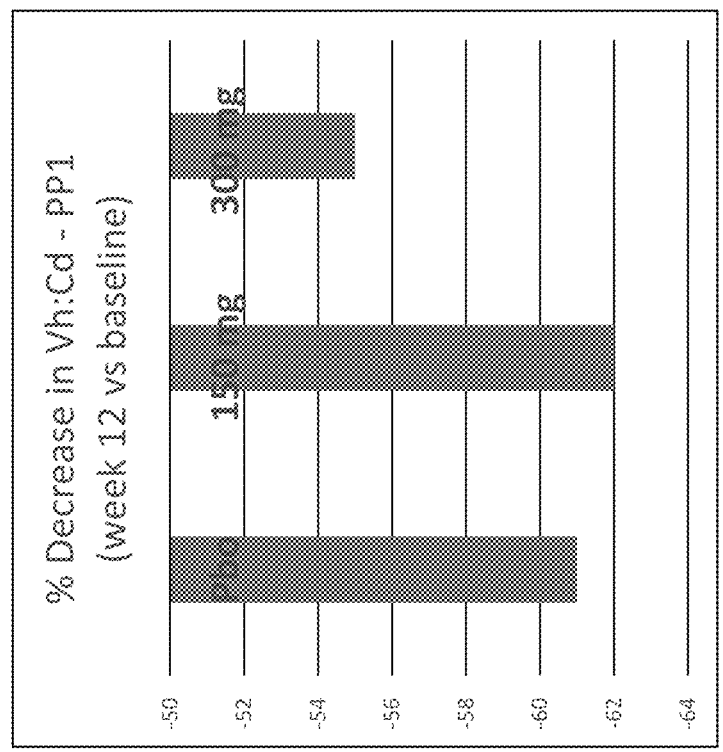
FIG. 6A shows relative (%) decrease in VH:CD from baseline in VH:CD (PP1 Population).

In the PP1 population (i.e., subjects who underwent GC), the relative reduction of VH:CD from baseline was ~61% in the placebo group, ~62% in the 150 mg group (p=0.7 compared with placebo), and ~55% in 300 mg group (p=0.34, 6.4% difference from placebo). The findings are summarized in Table 3 and FIGS. 6A and 6B.

TABLE 3

Statistical Analysis Results of Relative (%) Change from Baseline in VH:CD ratio (PP1 Population)

| | Estimate | SE | t value | p value | 95% CL |
|---|---|---|---|---|---|
| AMG 714 150 mg vs placebo | −2.49 | 7.10 | −0.35 | 0.7271 | −16.82, 11.83 |
| AMG 714 300 mg vs placebo | 6.39 | 6.67 | 0.96 | 0.3438 | −19.85, −7.07 |

SE: standard error.
CL: confidence limit.

In the PP2 population, the placebo group (n=4) had an average decrease of 16% in VH:CD, the 150 mg group (n=5) had a decrease of 6%, and the 300 mg group (n=2) had an average decrease of 3%, respectively.

Secondary Efficacy Analyses

Figure 7B:
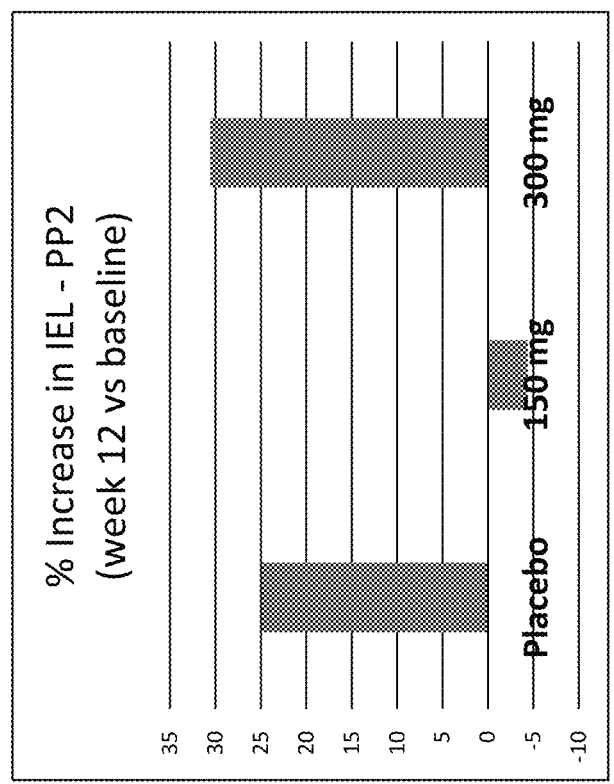
FIG. 7B shows relative change from baseline in IEL (PP2 Population).
Figure 7A:
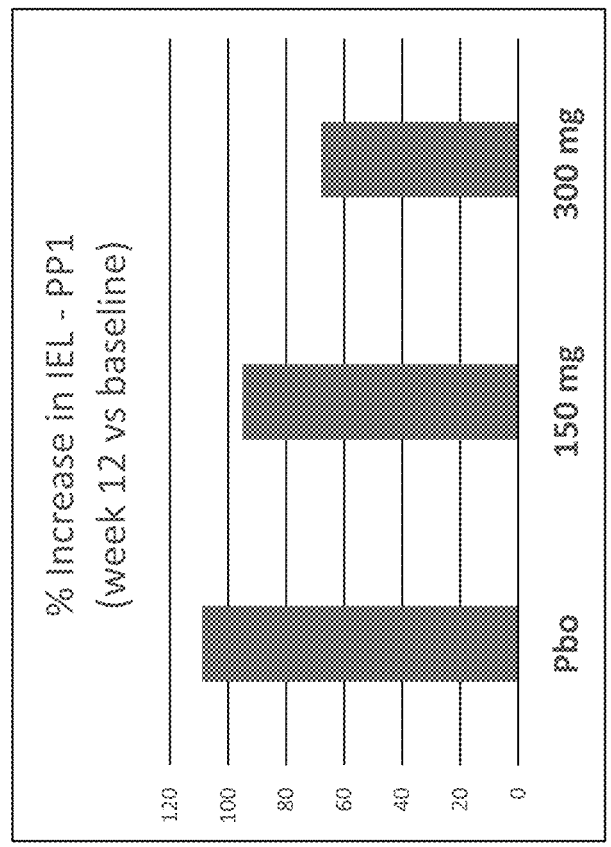
FIG. 7A shows relative (%) increase from baseline in IEL (PP1 Population).

Attenuation of Gluten-Induced Small Intestinal Mucosal Inflammation, Measured with IEL Density As shown in FIG. 7A, analysis of the IEL density showed that the relative increase from baseline in IEL was 109% in the placebo group, 95% in the 150 mg AMG 714 group (14% difference from placebo, p=0.5), and 68% in the 300 mg group (a 41% difference from placebo, p=0.03). The difference between placebo and 300 mg AMG 714 was statistically significant.

An ad hoc analysis showed that the proportion of patients who had less than 50% increase from baseline in IEL was 13% in the placebo group, 27% in the 150 mg group, and 50% in the 300 mg group.

In PP2, the placebo group (n=4) had an average increase of 25% in IEL, the 150 mg group (n=5) had a decrease of 4%, and the 300 mg group (n=2) had an average increase of 30.6%. In the 300 mg group, the 2 patients had dramatic variation in IEL change from baseline: 1 patient had a 2.2% increase and the other patient a 59% increase.

Attenuation of Gluten-Induced Small Intestinal Mucosal Morphological Injury Using a Grouped Classification of Marsh Score There was no difference in Marsh scores across groups.

Attenuation of Gluten-Induced Clinical Symptoms: CeD-PRO

The CeD-PRO is the only fully validated Patient Reported Outcome in celiac disease.

In PP1, both AMG 714 dose groups saw a dose-related reduction compared with the placebo. The CeD-PRO score change baseline was 0.81 in the placebo group, 0.5 in the 300 mg group (p=0.02), and 0.64 in the 150 mg group (p=0.3).

Figure 8:
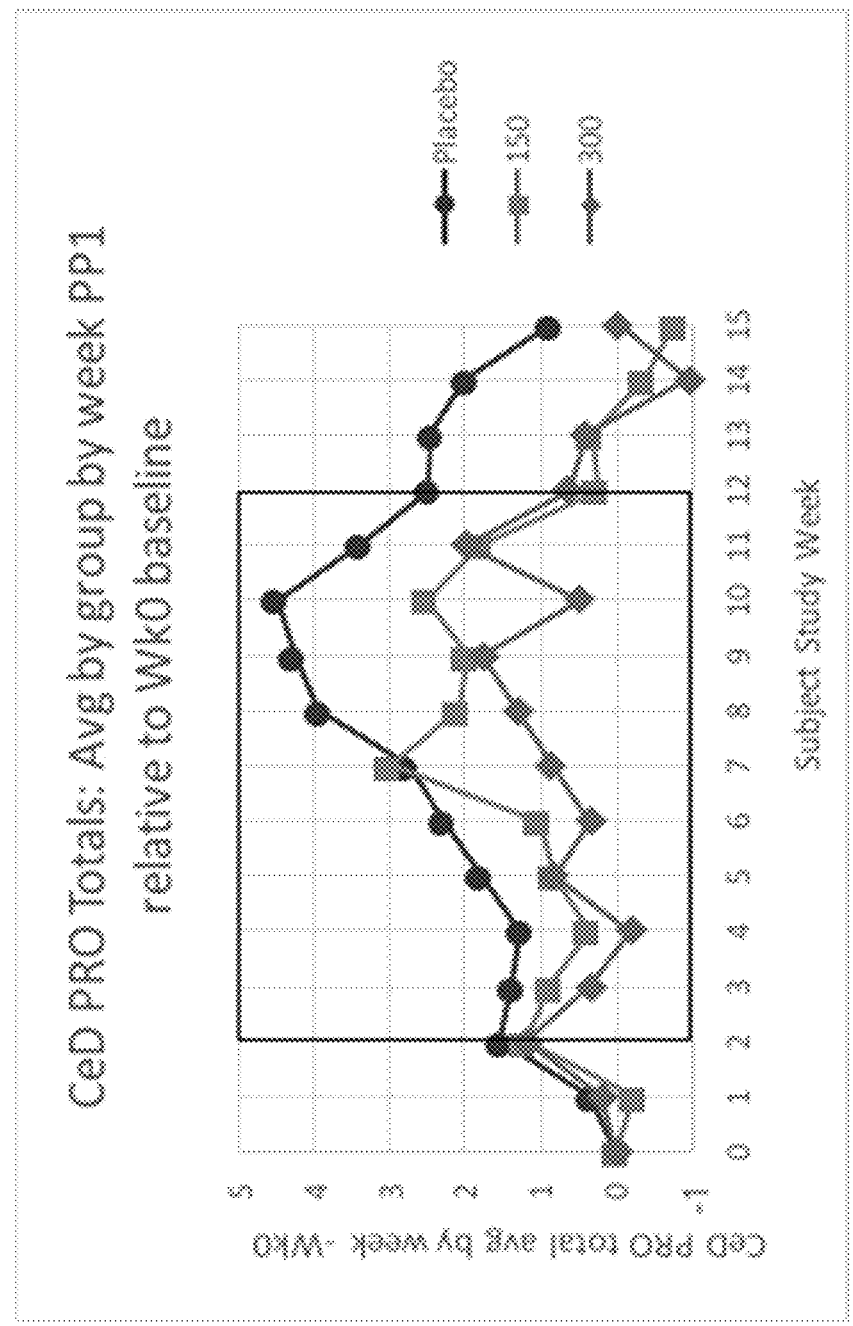
FIG. 8 shows mean CeD-PRO scores and change scores over time (PP1 Population).

As shown in FIG. 8, AMG 714 300 mg appears to have blunted the symptoms worsening caused by gluten over time. Some intermediate time points were statistically significant.

Attenuation of Gluten-Induced Clinical Symptoms: CeD-GSRS

Figure 9:
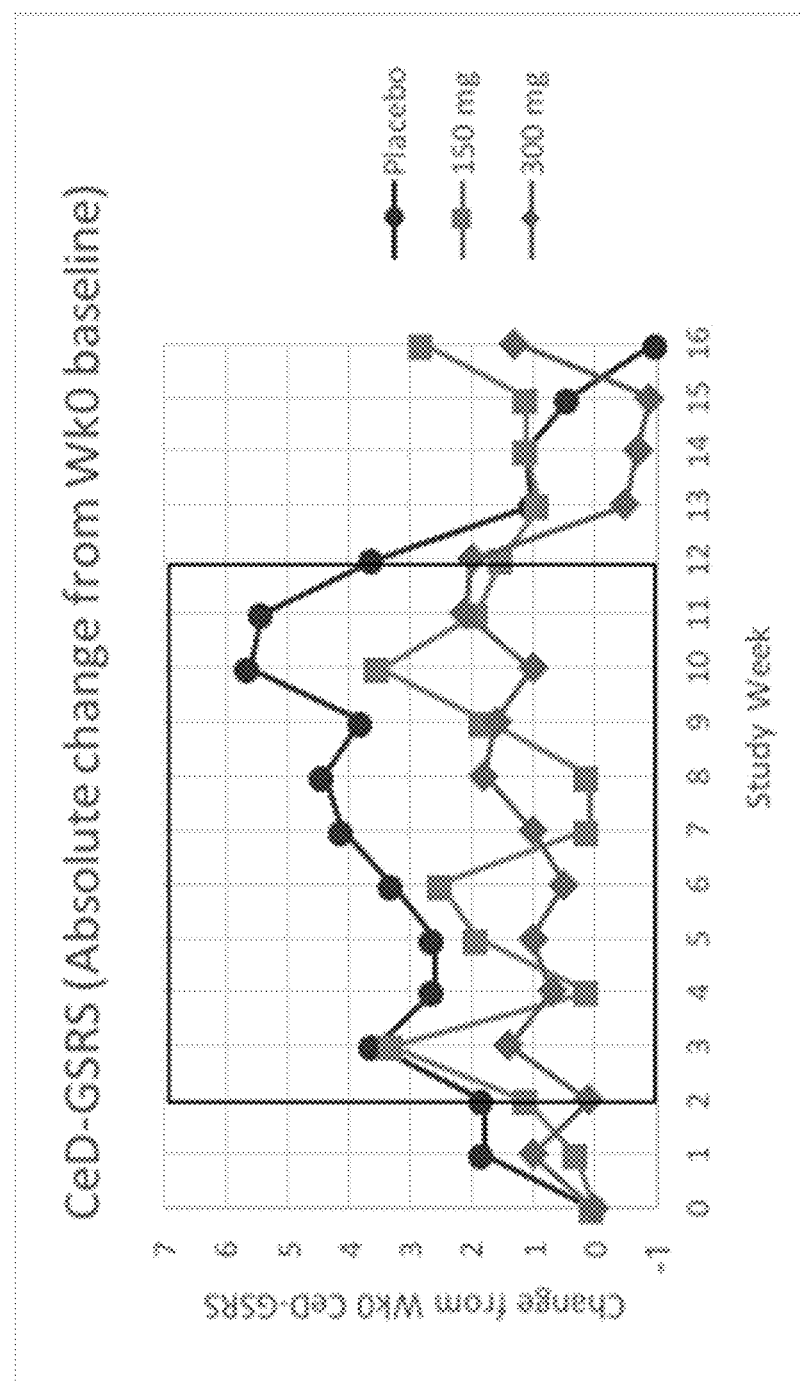
FIG. 9 shows mean CeD-GSRS scores and change scores over time (PP1 Population).

In PP1, both AMG 714 dose groups saw a reduction of symptoms compared with placebo. Subjects on 300 mg had approximately 84% reduction in the mean Cell-GSRS score (mean score=0.46) compared with subjects on placebo (mean score=2.97), which was not significant (p=0.07). The difference in mean CeD-GSRS scores between placebo (mean score=2.97) and 150 mg (mean score=0.96) was not statistically significant (p=0.17), but was numerically in favor of the active treatment group. As shown in FIG. 9, 300 mg appears to have blunted symptom worsening caused by gluten exposure over time.

In PP2 with little or no GC, the differences in CeD-GSRS also favored 150 mg over placebo, with the 150 mg group showing no increase in CeD-GSRS (mean score=−0.6), even though the difference from placebo (mean score=5.96) was not significant given the sample size (p=0.17). The differences were larger between Week 5 and Week 10. For the 300 mg group, there was no effect given discrepancies between the responses in the two patients in this group.

The GSRS results (not shown) tracked the CeD-GSRS closely, as expected, with p values of 0.11-0.17 for absolute and relative change from baseline, respectively, in the PP1 300 mg group.

Attenuation of Gluten-Induced Clinical Symptoms: BSFS

Figure 10:
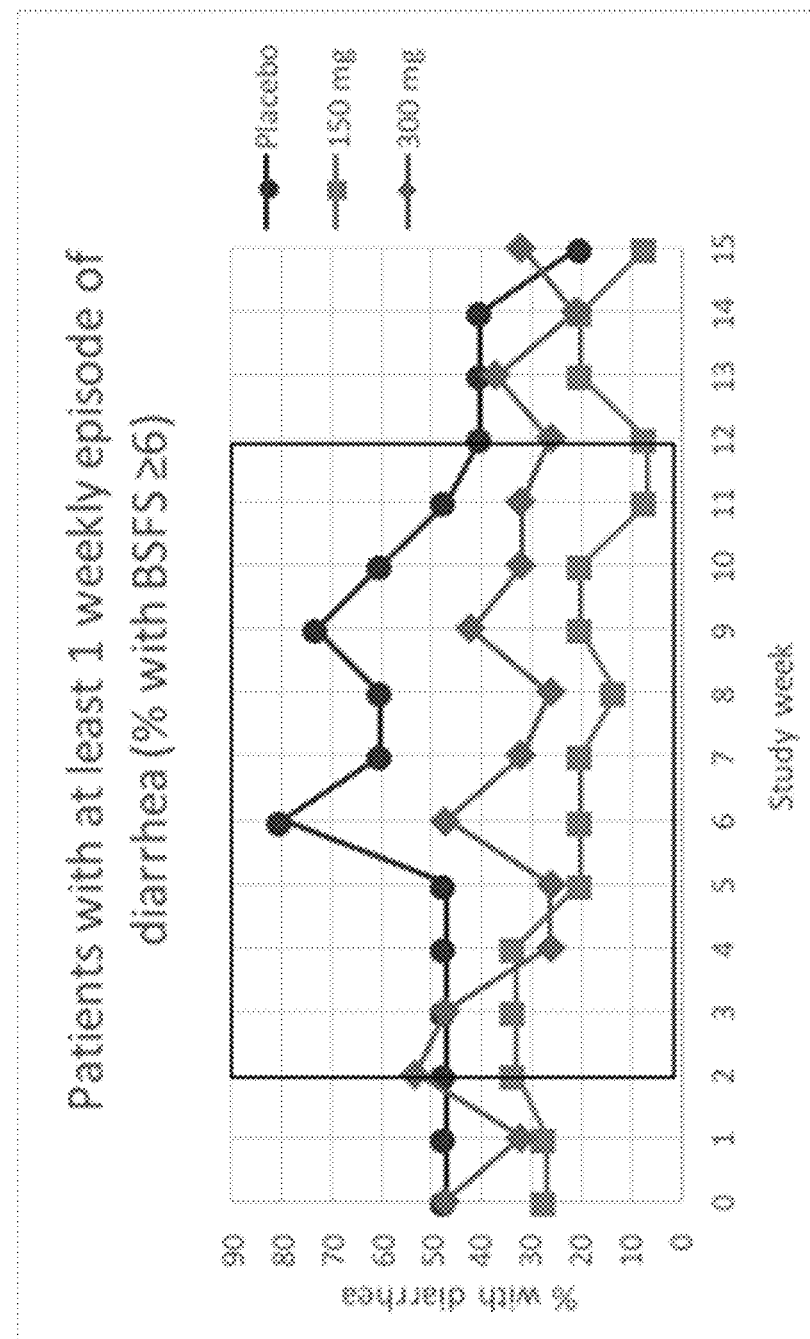
FIG. 10 shows proportion of subjects with at least 1 episode of diarrhea per week (PP1 Population).
Figure 11:
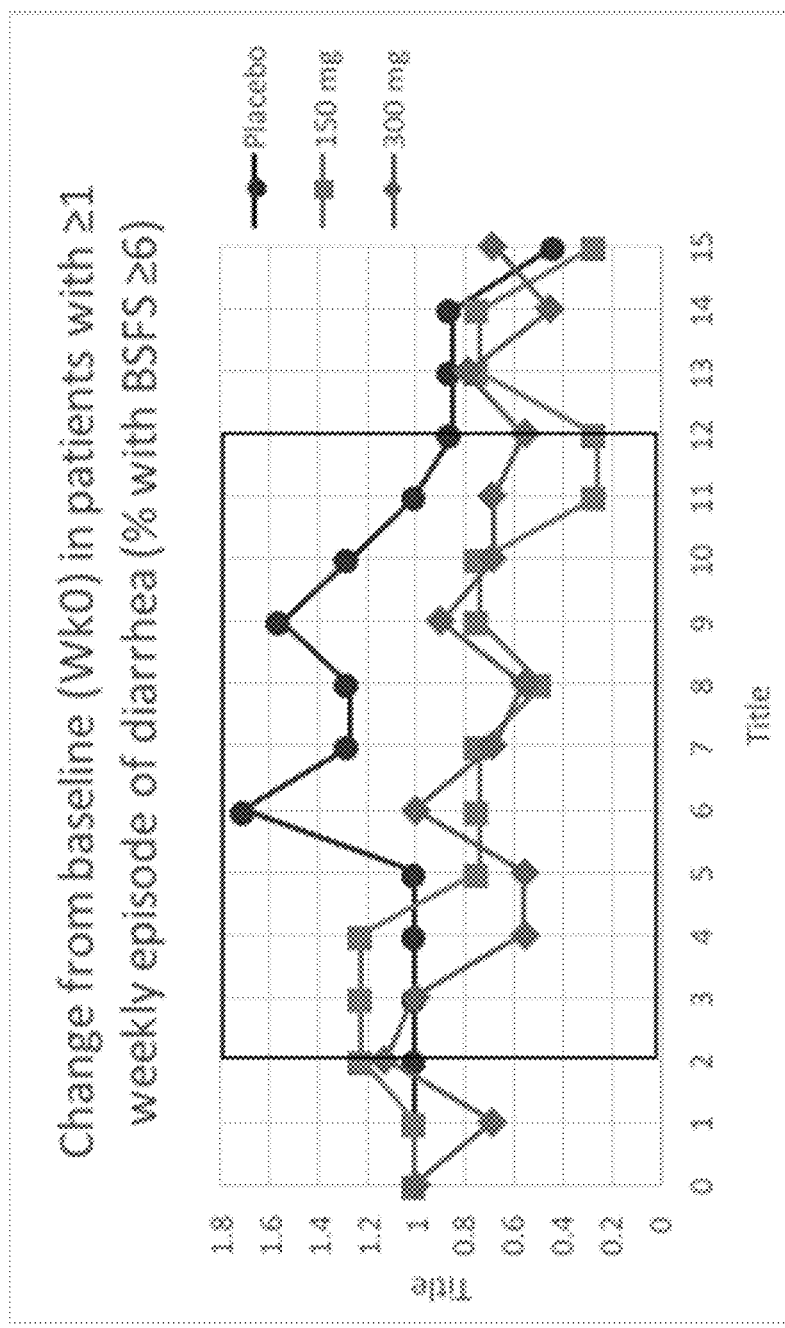
FIG. 11 shows change from baseline in proportion of subjects with at least 1 episode of diarrhea per week (PP1 Population).

There were fewer reports of loose stools BSFS (Types 5, 6, and 7) in subjects in both the 150 mg and 300 mg AMG 714 groups compared to placebo. The mean number of weeks without diarrhea, defined as BSFS Type 6 or 7, was lower in the AMG 714 groups compared with placebo (FIGS. 10 and 11).

Attenuation of Gluten-Induced Serum Anti-DGP IgA and IgG

Figure 12:
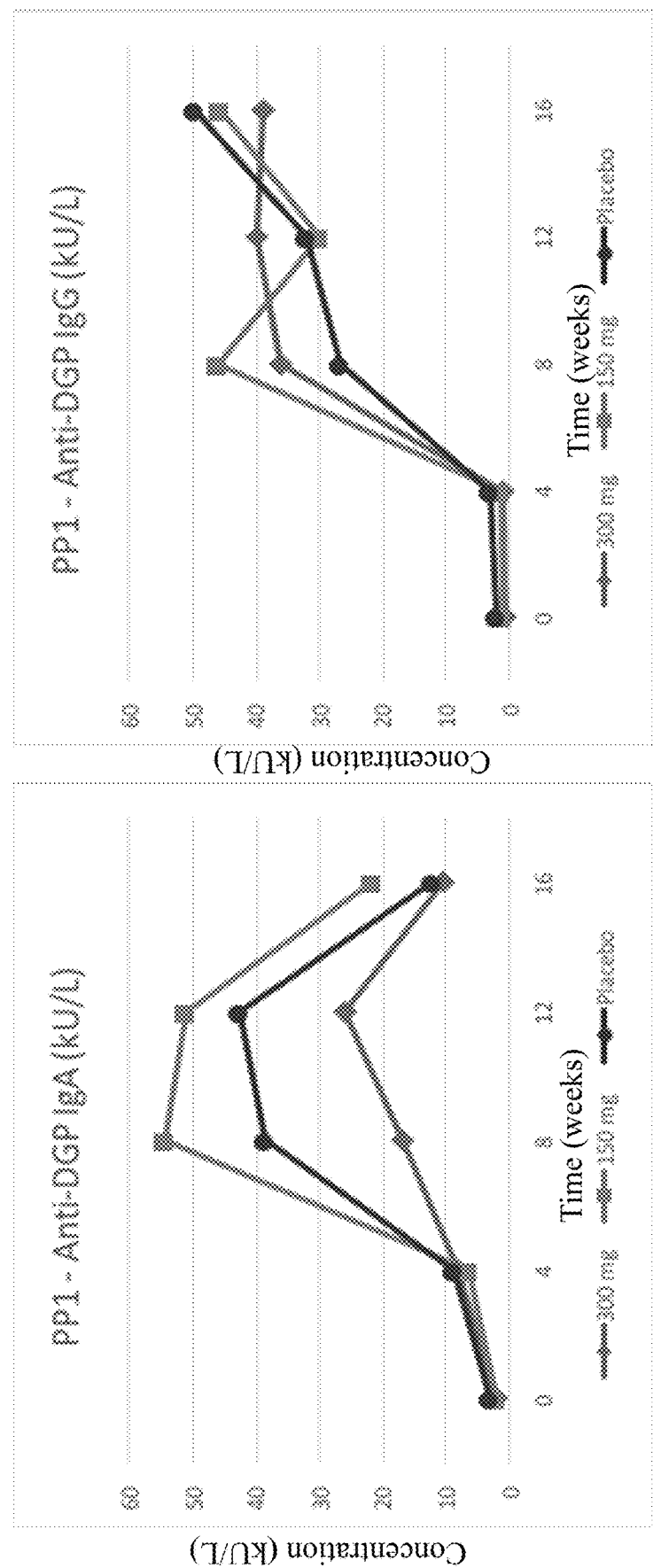
FIG. 12 shows anti-DGP IgA and IgG antibody levels over time (PP1 Population).

The anti-DGP IgA and IgG developed in many subjects in PP1 (FIG. 12), and not in any subject in PP2, which was an expected outcome given that PP1 underwent gluten challenge while PP2 did not.

AMG 714 300 mg had a trend towards inhibition of the anti-DGP IgA response and blunted the anti-DGP IgG response (slower than IgA) by the end of the study in PP1.

Attenuation of Gluten-Induced Serum Anti-tTG IgA

Figure 13:
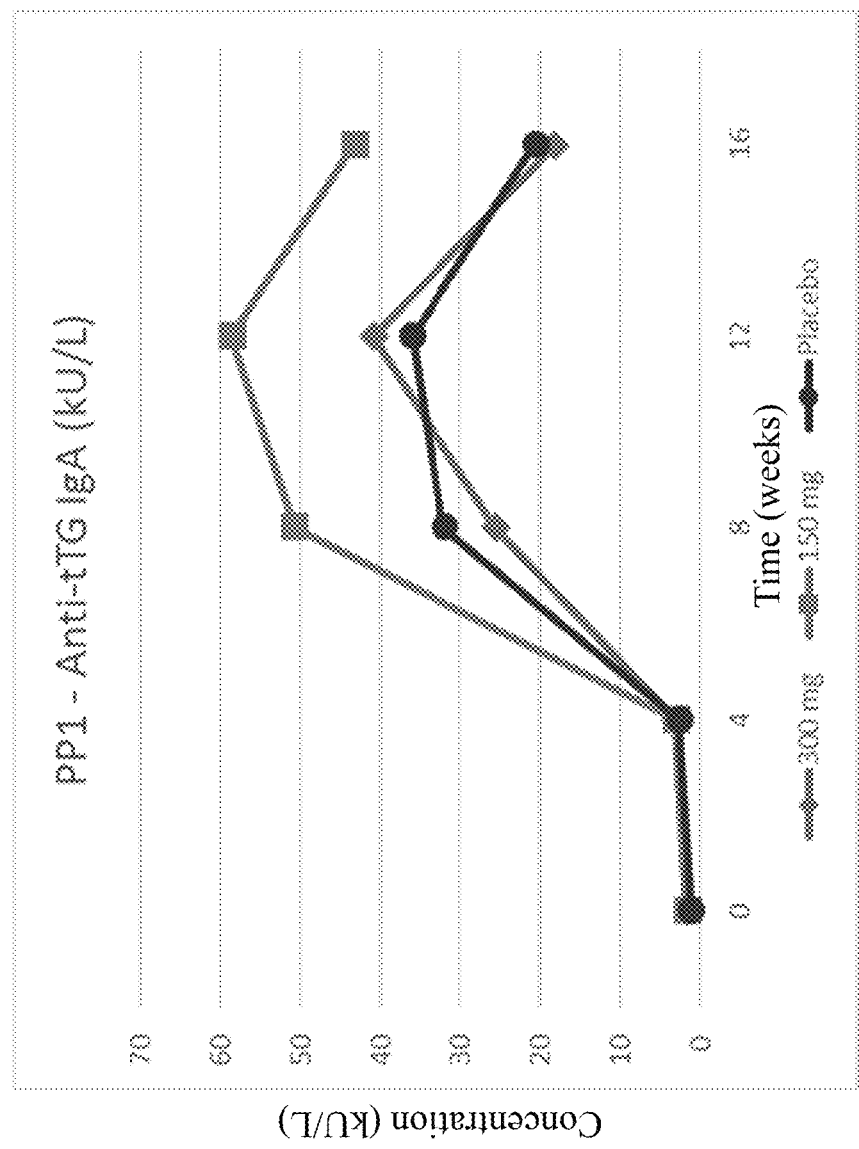
FIG. 13 shows Anti-tTG IgA antibody levels over time (PP1 Population).

Consistent with a mouse model of IL-15-driven celiac disease (humanized HLA-DQ8-transgenic mice overexpressing IL-15 to the same level of celiac disease patients, and fed gluten) which shows that only anti-DGP antibodies but not anti-tTG are dependent on IL-15, AMG 714 did not alter the production of anti-tTG IgA triggered by daily GC and, in the 150 mg group, the titers were significantly more elevated than in the placebo group (p=0.0037), with no observed differences between the 300 mg and placebo (FIG. 13).

Pharmacokinetics

Figure 14:
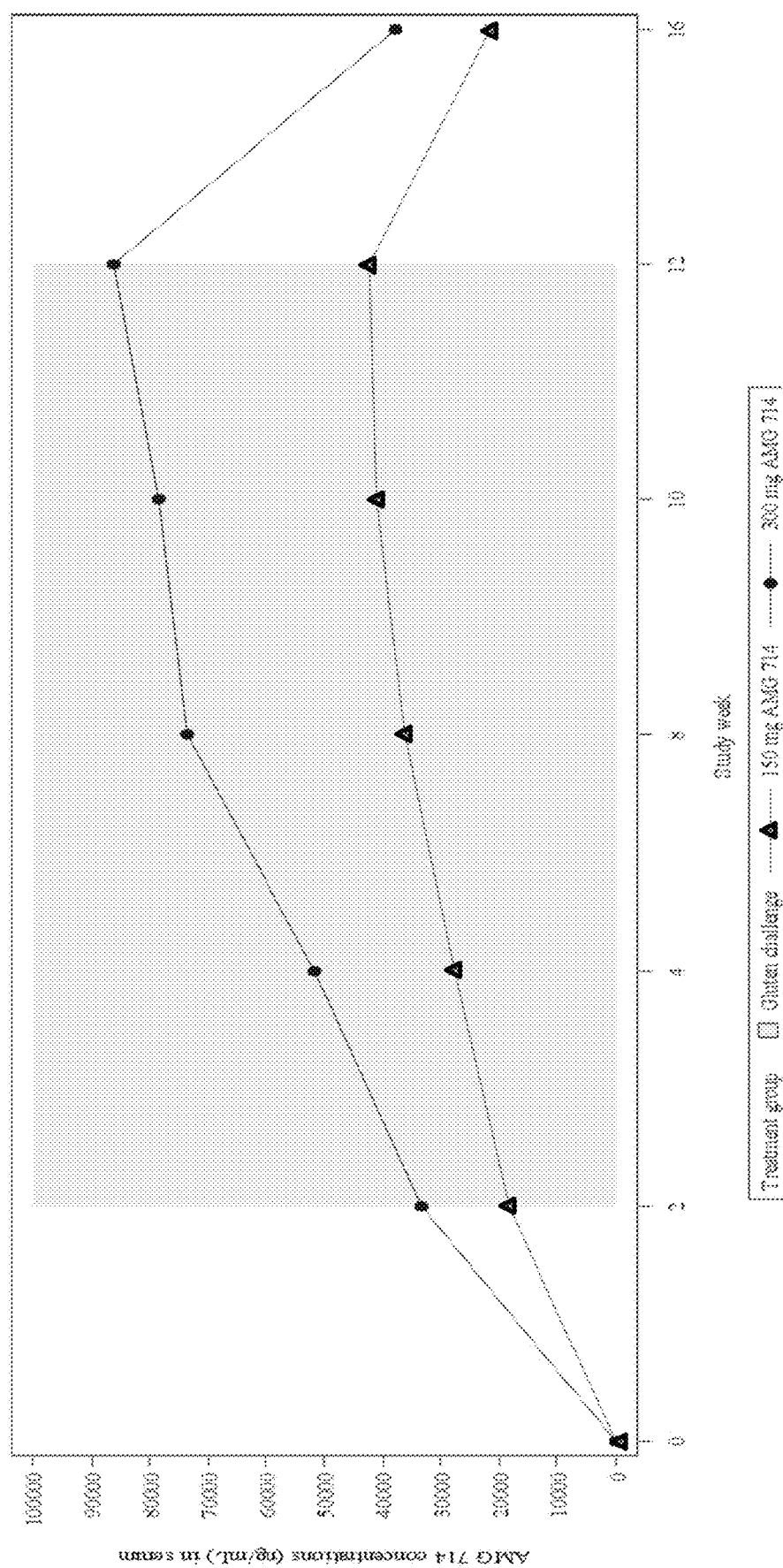
FIG. 14 shows AMG 714 serum concentrations by dose levels (PP1 Population).
Figure 15:
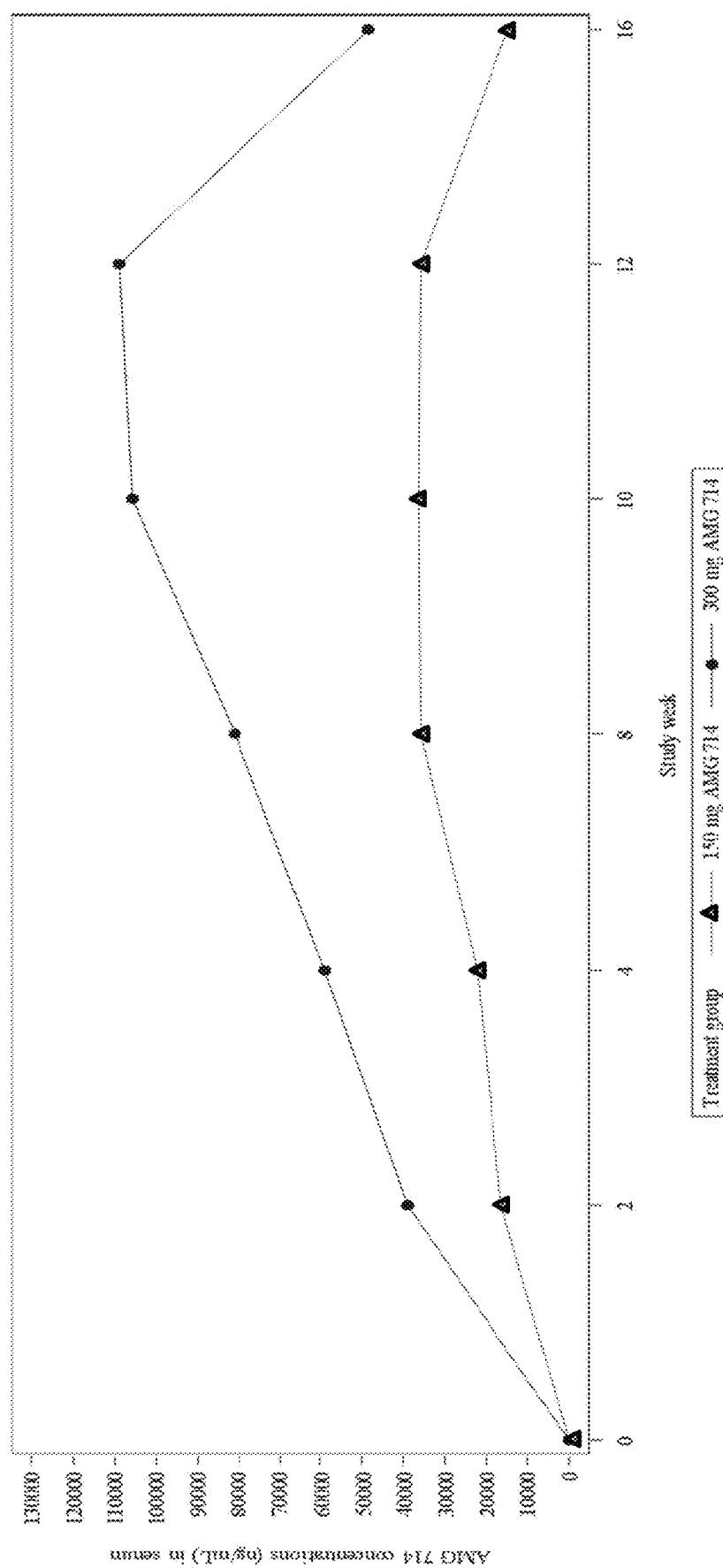
FIG. 15 shows AMG 714 serum concentrations by dose levels (PP2 Population).

The PK profile of AMG 714 in this patient population was favorable (FIGS. 14 and 15; Table 4). The exposure to AMG 714 in patient in this trial was double the exposure observed in the previous psoriasis study (ClinicalTrials.gov Identifier: NCT00443326) with the same dosing regimen. This increased exposure can be explained by the higher proportion of female subjects and normal weight (approximately 70 kg) in enrolled celiac patients, as compared with enrolled psoriasis patients, who are predominantly men with average body weight of approximately 95 kg. In addition to weight difference, the clearance of monoclonal antibodies in men is approximately 20% higher than that in women.

TABLE 4

Summary of AMG 714 Serum Concentrations by Dose and Visit

| Dose | Visit | Week | N | Mean | SD | Median | Min | Max |
|---|---|---|---|---|---|---|---|---|
| 150 mg | 2 | 2 | 21 | 18 | 4.5 | 19.5 | 10.3 | 24.1 |
|  | 3 | 4 | 20 | 26.4 | 9.2 | 28.1 | 12.3 | 43.3 |
|  | 5 | 8 | 20 | 36.1 | 11 | 38.8 | 18.8 | 48.9 |
|  | 6 | 10 | 19 | 40.1 | 12.9 | 42.4 | 15.3 | 58.6 |
|  | 7 | 12 | 20 | 40.8 | 14.7 | 45 | 16.4 | 64.9 |
|  | 8 | 16 | 22 | 19.1 | 9 | 18.6 | 5 | 38.1 |
| 300 mg | 2 | 2 | 21 | 33.7 | 12.6 | 34.7 | 12.3 | 59.4 |
|  | 3 | 4 | 19 | 52.4 | 17.4 | 51.3 | 22.5 | 83.8 |
|  | 5 | 8 | 20 | 74.3 | 24.4 | 73.8 | 35.2 | 120 |
|  | 6 | 10 | 20 | 81.1 | 27.8 | 85.7 | 42.3 | 131 |
|  | 7 | 12 | 20 | 88.3 | 32.3 | 84.5 | 43.2 | 158 |
|  | 8 | 16 | 22 | 39 | 13.6 | 36.7 | 15.6 | 58.1 |

PK/PD Correlation

There seems to be an association between drug exposure and efficacy.

Figure 16:
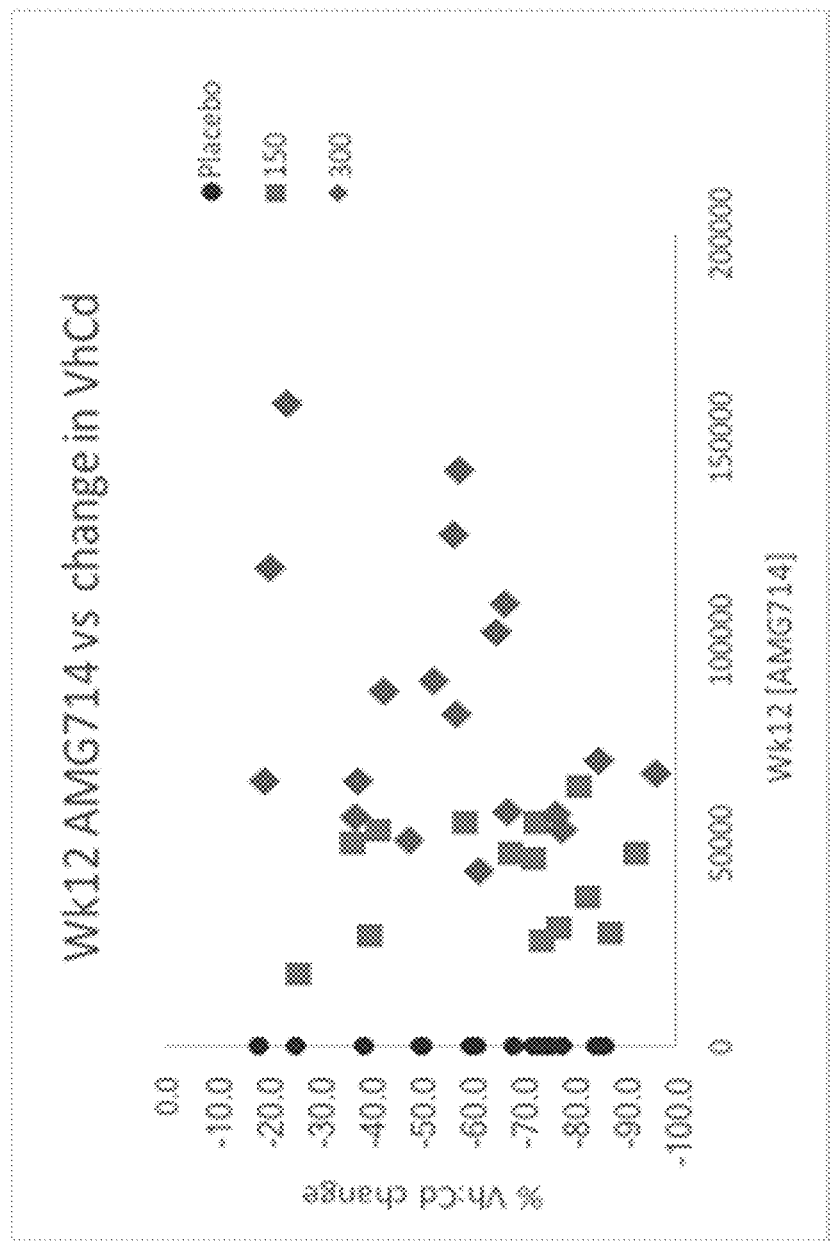
FIG. 16 shows scatter plot of AMG 714 concentrations at Week 12 against relative (%) change from baseline in VH:CD ratio.
Figure 17:
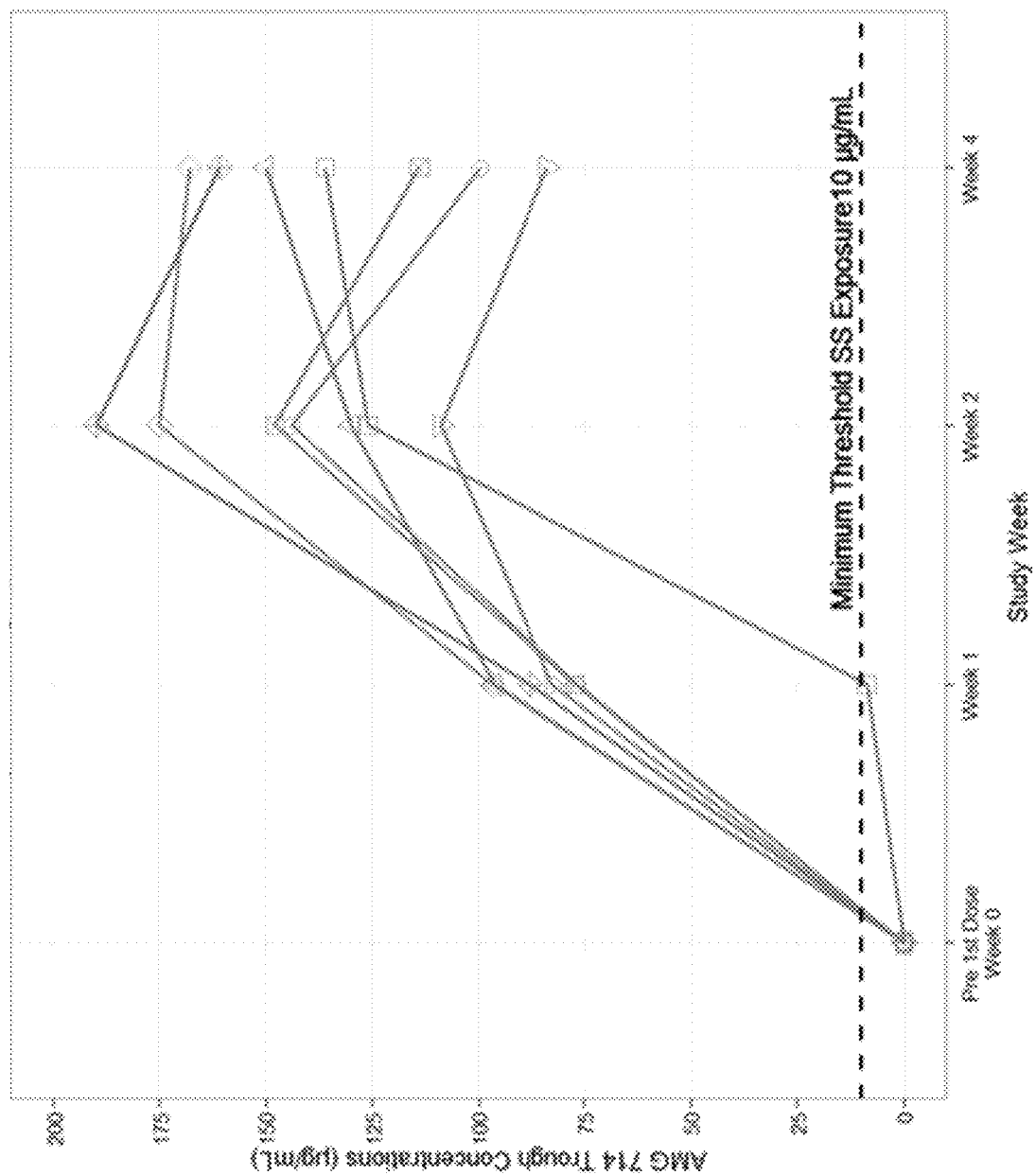
FIG. 17 shows AMG 714 trough concentrations (μg/mL) from Example 2 by subject PK interim analysis of trough (pre-dose, time=0) concentrations.

Preliminary exploration of PK/PD correlations suggest an exposure/response association at the 300 mg dose level (FIGS. 16 and 17). This association was driven by overlapping exposures for the 150 mg and 300 mg treatment groups, with 300 mg exposures that were greater than the range observed in the 150 mg arm showing larger responses in multiple endpoints. This suggests that a higher dose could reach greater effect sizes.

Safety Analyses

Summary of Adverse Events

Adverse events that occurred before treatment administration, i.e., during the screening period, occurred in 46.8% of all subjects. None of the AEs prior to treatment were SAEs or resulted in discontinuation.

Treatment-emergent AEs, i.e., those that occurred after the study treatment was initiated, that occurred in all subjects who received at least 1 dose of the study drug, are summarized in Table 5 below.

TABLE 5

Subject Incidence of Treatment-Emergent Adverse Events (TEAE) During Treatment Period, Visit 1 to Visit 8 (ITT Population)

| | n (%) | | | |
|---|---|---|---|---|
| | AMG 714 150 mg N = 22 | AMG 714 300 mg N = 21 | Placebo N = 19 | Total N = 62 |
| At least 1 TEAE | 21 (95.5) | 20 (95.2) | 19 (100.0) | 60 (96.8) |
| At least 1 TEAE related to study drug* | 10 (45.5) | 12 (57.1) | 7 (36.8) | 29 (46.8) |
| At least 1 SAE | 0 | 0 | 0 | 0 |
| Discontinued due to AE | 1 (4.5) | 1 (4.8) | 0 | 2 (3.2) |

*Related includes "definitely" and "probably" related.

Adverse events that occurred after treatment administration were reported by 96.8% of ITT subjects. None of the TEAEs were serious. Two subjects discontinued the study due to AEs (one in 150 mg and one in 300 mg). During the treatment period, 95.5%, 95.2%, and 100.0% of the subjects in the 150 mg AMG 714, 300 mg AMG 714, and placebo groups, respectively, reported at least 1 TEAE. No difference was observed in overall adverse event reports between AMG 714 and placebo treatment.

Exploratory Analyses

Physician Global Assessment (PGA)

PGA is a dichotomized endpoint, in which a PGA score of <2 is considered treatment success and a PGA score of >2 is considered treatment failure. The estimate of effect is the proportion of subjects considered success and failure.

The proportion of subjects with PGA >2 was 33% in the placebo group, compared with 13.3% in the AMG 714 150 mg group (p=0.390, estimated treatment difference [95% CI]: −20% [−56%, 16%]) and 0% in the 300 mg group (p=0.013, estimated treatment difference [95% CI]: −33% [−63%, −3%]).

No clear trends were observed in PP2, though at the end of the study, both subjects in the 300 mg group were graded 1 (no disease activity), and 1 patient each in the 150 mg and the placebo groups was also graded 1.

Serum IL-15 Levels

Serum IL-15 was not entirely eliminated by 300 mg AMG 714 in PP1 but was in PP2, which suggests that a higher dose of AMG 714 may have been necessary to counteract the effect of GC. There was an association between the serum levels of IL-15 and the decrease in VH:CD.

TABLE 7

Serum Concentrations of IL-15 from Visit
1 to Visit 7 by Treatment Group (PP1)

| AMG 714 Dose | Serum IL-15 Concentration (pg/ml) | | |
|---|---|---|---|
| | Mean | SD | Peak |
| 0 | 9.7 | 24.5 | 126.7 |
| 150 mg | 16.2 | 36.8 | 139.6 |
| 300 mg | 6.0 | 17.2 | 83.9 |
| All | 14.2 | 27.6 | 139.6 |

TABLE 8

Serum Concentrations of IL-15 from Visit
1 to Visit 7 by Treatment Group (PP2)

| AMG 714 Dose | Serum IL-15 Concentration | | |
|---|---|---|---|
| | Mean | SD | Peak |
| 0 | 11.0 | 27.4 | 101.9 |
| 150 mg | 9.0 | 16.6 | 65.7 |
| 300 mg | 0.2 | 0.7 | 2.3 |
| All | 8.0 | 20.1 | 101.9 |

Example 2: Phase 2a Study to Evaluate Efficacy
and Safety of AMG 714 in Adult Patients with
Type II Refractory Celiac Disease In an exemplary clinical trial the efficacy and safety of AMG 714 can be studied in adult patients with Type II Refractory Celiac Disease. The primary objective of this study will be to assess the efficacy of AMG 714 in treating RCD-II in adult patients. The secondary object of this study will be to assess the safety and tolerability of AMG 714 when administered to adult patients with RCD-II. The exploratory objectives of this study will be to assess the pharmacokinetics (PK), pharmacodynamics (PD), and PK/PD correlations of AMG 714.

Primary outcome/endpoint measures include immunological response, e.g., reduction from baseline in the % of aberrant small bowel intestinal intraepithelial lymphocytes (surface CD3− intracellular CD3+). Time Frame: Baseline and 12 weeks. Reduction from baseline in the % of aberrant intestinal intraepithelial lymphocytes can be measured by, e.g., flow cytometry after small intestinal biopsy collection.

Secondary outcome/endpoint measures:
(1) Histological response: Improvement from baseline in small intestinal morphology as measured by the Villous Height to Crypt Depth (VH:CD) ratio in intestinal biopsy material. Time Frame: Baseline and 12 weeks.
(2) Clinical response: Change from baseline in clinical symptoms as measured by the Gastrointestinal Symptom Rating Scale (GSRS). Time Frame: Baseline and 12 weeks.

Other outcome/endpoint measures include safety and tolerability: Number of participants with treatment-related adverse events as assessed by Common Terminology Criteria for Adverse Events (CTCAE). Time Frame: 12 weeks. The frequency and nature of adverse events can be collected and analyzed.

Study Design

The protocol is designed to be a Phase 2a randomized, double-blind, placebo-controlled, parallel group study to evaluate the efficacy and safety of AMG 714 for the treatment of adult patients with RCD-II.

All subjects who meet the study entry criteria can be randomized at a 2:1 ratio to receive either 8 mg/kg AMG 714 or placebo every 2 weeks for a total of 7 times over 10 weeks, with evaluation of the primary endpoint at Week 12. AMG 714 or placebo can be administered at the clinical site in a double-blind fashion via intravenous (IV) infusion over 120 minutes.

Subjects will be expected to maintain total adherence to a strict gluten-free diet (GFD) from 6 months before randomization through the final study visit (Visit 9, Week 16/Day 112).

The final study dose will be administered at Visit 7 (Week 10/Day 70). An end-of-study efficacy visit will be conducted at Visit 8 (Week 12/Day 84). The final study visit will be conducted 6 weeks after the last dose of study drug at Visit 9 (Week 16/Day 112)

All study subjects can undergo upper gastrointestinal endoscopy with mucosal biopsy prior to baseline (i.e., prior to Visit 1, Week 0/Day 0) and within 7 days of Visit 8 (Week 12/Day 84) in order to assess changes from baseline in aberrant and abnormal IELs, VH:CD ratio, TCR clonality, Marsh score and total IEL counts.

Safety can be monitored on an ongoing basis and subjects may undergo unscheduled visits for safety reasons, if needed. Safety will be assessed throughout the study by clinical laboratory tests, physical examination, vital sign and AE monitoring.

Subject Inclusion Criteria:
Confirmed diagnosis of refractory celiac disease Type 2 (RCD-II)
Greater than 20% aberrant intraepithelial lymphocytes (IEL) as assessed by flow cytometry
On a gluten-free diet for at least 6 months
Avoid pregnancy
Exclusion Criteria:
Enteropathy-Associated T cell Lymphoma (EATL)
Infections
Immune suppression
Clinically significant co-morbidities The proposed dose of 8 mg/kg IV for 10 weeks, once every 2 weeks (q2w) with an extra dose at week 1, can account for the presumed protein-losing enteropathy typical of RCD-II (up to 40% protein loss can be expected based on albumin levels in RCD-II patients) and for the larger target organ area (small bowel as compared to more localized joints).

A pharmacokinetic interim analysis has been completed for the review of AMG 714 concentrations through week 4 of dosing for the first 10 subjects randomized to assure a minimal steady-state threshold exposure of ≥10 µg/mL is achieved and maintained.

As shown in FIG. 17, the trough level pre-dose on week 4 is, on average, 130 ug/ml, slightly above the 90 ug/ml predicted. All patients, including several with severe hypoalbuminemia, are above the 10 ug/ml targeted. Thus, the concentrations of AMG 714 are close to what was expected based on healthy subjects (our PK reference for IV formulation).

Various aspects of the present disclosure may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments. Also, the phraseology and terminology used herein is for the purpose of description and should not be regarded as limiting.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for the use of the ordinal term) to distinguish the claim elements.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items. "Consisting essentially of" means inclusion of the items listed thereafter and which is open to unlisted items that do not materially affect the basic and novel properties of the invention.

INCORPORATION BY REFERENCE

The ASCII text file submitted herewith via EFS-Web, entitled "A2082US.txt" created on Jun. 15, 2016, having a size of 4,622 bytes, is hereby incorporated by reference in its entirety.

All publications, patents and sequence database entries mentioned herein are hereby incorporated by reference in their entireties as if each individual publication or patent was specifically and individually indicated to be incorporated by reference.

REFERENCES

Abadie V, Jabri B. Immunol Rev. 2014; 260:221-34.
Anthony S M, Howard M E, Hailemichael Y, et al. PLoS One. 2015; 10:e0120274.
Baslund B, Tvede N, Danneskiold-Samsoe B, et al. Arthritis Rheum. 2005; 52(9):2686-92.
Blaser B W, Roychowdhury S, Kim D J, et al. Blood. 2005; 105(2):894-901.
Brar P, Lee S, Lewis S, et al. Am J Gastroenterol. 2007; 102:2265-9.
Catassi C, Fabiani E, Iacono G, et al. Am J Clin Nutr. 2007; 85(1):160-6.
Conti F, Frappier J, Dharancy S, et al Transplantation. 2003; 76(1):210-6.
Cranney A, Zarkadas M, Graham I D, et al. Dig Dis Sci. 2007; 52(4):1087-95.
DePaolo R W, Abadie V, Tang F, et al. Nature. 2011; 471:220-4.
Fehniger T A, Caligiuri M A. Blood. 2001; 97:14-32.
Gianfrani C, Auricchio S, Troncone R. Immunol Lett. 2005; 99(2):141-145.
Gibert A, Espadaler M, Canela A, et al. Eur J Gastroenterol Hepatol 2006; 18:1187-1195.
Goerres M S, Meijer J W, Wahab P J, et al. Aliment Pharmacol Ther 2003; 18:487-94.
Green P H, Cellier C. N Engl J Med. 2007; 357(17):1731-43
Hopper A D, Cross S S, Hurlstone D P, et al. Br Med Journal. 2007; 334(7596):729
Kennedy M K, Glaccum M, Brown S N, et al. J Exp Med. 2000; 191:771-780.
Korneychuk N, Ramiro-Puig E, Ettersperger J, et al. Gastroenterology. 2014; 146:1017-27.
Lebrec H, Horner M J, Gorski K S, et al. J Immunol. 2013; 191(11):5551-8.
Lebwohl B, Granath F, Ekbom A, et al. Ann Intern Med. 2013; 159(3):169-75.
Lee S K, Lo W, Memeo L, Rotterdam H, Green P H. Gastrointest Endosc. 2003; 57(2):187-91.
Litinskiy M B, Nardelli B, Hilbert D M, He B, Schaffer A, Casali P, Cerutti A. Nat Immunol. 2002; 3(9):822-829.
Lodolce J P, Boone D L, Chai S, Swain R E, Dassopoulos T, Trettin S, Ma A. Immunity. 1998; 9(5):669-676.
Lundin, Knut E.a., and Armin Alaedini. Gastrointestinal Endoscopy Clinics of North America 22.4 (2012): 723-34.
Malamut G, El Machhour R, Montcuquet N, et al. J Clin Invest. 2010; 120:2131-43.
McInnes I B, Gracie J A. Curr Opin Pharmacol. 2004; 4(4):392-397.
Meresse B, Malamut G, Cerf-Bensussan N. Immunity. 2012; 36:907-19.
Midhagen G, Hallert C. Am J Gastroenterol. 2003; 98:2023-6.
Nijeboer P, Malamut G, Bouma G, et al. Dig Dis. 2015; 33:227-230.
Park C S, Yoon S O, Armitage R J, Choi Y S. J Immunol. 2004; 173(11):6676-6683.
Rubio-Tapia A, Hill I D, Kelly C P, et al. Am J Gastroenterol. 2013; 108:656-76.
Shah S, Akbari M, Vanga R, et al. Am J Gastroenterol. 2014; 109(9):1304-11.
Sharaiha R Z, Lebwohl B, Reimers L, et al. Cancer. 2012; 118:3786-92.
Schluns K S, Stoklasek T, Lefrancois L. Int J Biochem Cell Biol. 2005; 37(8):1567-1571.
Taavela, Juha, Kalle Kurppa, Pekka Collin, et al. Clinical Gastroenterology and Hepatology 11.2 (2013): 166-71.
Tack G J, Verbeek W H, Al-Toma A, et al. World J Gastroenterol 2011; 17:506-13.
Tack G J, Wondergem M J, Al-Toma A, et al. Bone Marrow Transplant 2011; 46:840-6.
van Wanrooij R L, Willer D M, Neefjes-Borst E A, et al. J Clin Immunol 2014; 34:828-35.
Verbeek W H, Schreurs M W, Visser O J, et al. Expert Rev Clin Immunol 2008; 4:205-19.
Yokoyama S, Watanabe N, Sato N, et al. Proc Natl Acad Sci USA 2009; 106: 15849-15854.
Yokoyama S, Takada K, Hirasawa M, et al. J Clin Immunol. 2011; 31(6):1038-44.

The invention claimed is:

1. A method of treating celiac disease or non-celiac gluten sensitivity in a subject in need thereof, comprising administering about 300 mg of an anti-IL-15 antibody or antigen-binding fragment thereof to the subject about once every 2 weeks, wherein said anti-IL-15 antibody or antigen-binding fragment thereof comprises a heavy chain variable region comprising complementarity determining regions (CDRs) set forth in SEQ ID NOs: 5-7, and a light chain variable region comprising CDRs set forth in SEQ ID NOs: 8-10.

2. The method of claim 1, wherein said anti-IL-15 antibody or antigen-binding fragment thereof comprises a heavy chain variable region comprising the amino acid sequence of SEQ ID NO: 2, and a light chain variable region comprising the amino acid sequence of SEQ ID NO: 4.

3. The method of claim 1, wherein said anti-IL-15 antibody or antigen-binding fragment thereof is administered by subcutaneous injection or intravenous injection.

4. A method of treating refractory celiac disease in a subject in need thereof, comprising administering about 300 mg of an anti-IL-15 antibody or antigen-binding fragment thereof to the subject about once every 2 weeks, wherein said anti-IL-15 antibody or antigen-binding fragment thereof comprises a heavy chain variable region comprising complementarity determining regions (CDRs) set forth in SEQ ID NOs: 5-7, and a light chain variable region comprising CDRs set forth in SEQ ID NOs: 8-10.

5. The method of claim 4, wherein said anti-IL-15 antibody or antigen-binding fragment thereof comprises a heavy chain variable region comprising the amino acid sequence of SEQ ID NO: 2, and a light chain variable region comprising the amino acid sequence of SEQ ID NO: 4.

6. The method of claim 4, further comprising administering an additional loading dose at week 1.

7. The method of claim 4, wherein said anti-IL-15 antibody or antigen-binding fragment thereof is administered by subcutaneous injection or intravenous injection.

* * * * *

SEQUENCE LISTING

<160> NUMBER OF SEQ ID NOS: 10

<210> SEQ ID NO 1
<211> LENGTH: 390
<212> TYPE: DNA

<213> ORGANISM: Homo sapiens

<400> SEQUENCE: 1

| | | | | | |
|---|---|---|---|---|---|
| gaggtgcagc | tggtgcagtc | tggagcagag | gtgaaaaagc | ccggggagtc | tctgaagatc | 60 |
| tcctgtaagg | tttctggata | cttctttacc | acctactgga | tcggctgggt | gcgccagatg | 120 |
| cccgggaaag | gcctggagta | tatggggatc | atctatcctg | gtgactctga | taccagatac | 180 |
| agcccgtcct | tccaaggcca | ggtcaccatc | tcagccgaca | agtccatcag | caccgcctac | 240 |
| ctgcagtgga | gcagcctgaa | ggcctcggac | accgccatgt | attactgtgc | gagaggggt | 300 |
| aactggaact | gctttgacta | ctggggccag | ggaaccctgg | tcaccgtctc | ctcagcctcc | 360 |
| accaagggcc | catcggtctt | ccccctggca | | | | 390 |

<210> SEQ ID NO 2
<211> LENGTH: 130
<212> TYPE: PRT
<213> ORGANISM: Homo sapiens

<400> SEQUENCE: 2

Glu Val Gln Leu Val Gln Ser Gly Ala Glu Val Lys Lys Pro Gly Glu
1               5                   10                  15

Ser Leu Lys Ile Ser Cys Lys Val Ser Gly Tyr Phe Phe Thr Thr Tyr
            20                  25                  30

Trp Ile Gly Trp Val Arg Gln Met Pro Gly Lys Gly Leu Glu Tyr Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Gly Asn Trp Asn Cys Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala
    130

<210> SEQ ID NO 3
<211> LENGTH: 357
<212> TYPE: DNA
<213> ORGANISM: Homo sapiens

<400> SEQUENCE: 3

| | | | | | |
|---|---|---|---|---|---|
| gaaattgtgt | tgacgcagtc | tccaggcacc | ctgtctttgt | ctccagggga | aagagccacc | 60 |
| ctctcctgca | gggccagtca | gagtgttagc | agcagctact | tagcctggta | ccagcagaaa | 120 |
| cctggccagg | ctcccaggct | cctcatctat | ggtgcatccc | gcaggccac | tggcatccca | 180 |
| gacaggttca | gtggcagtgg | gtctgggaca | gacttcactc | tcaccatcag | cagactggag | 240 |
| cctgaagatt | ttgcagtgta | ttactgtcag | cggtatggta | gctcacacac | ttttggccag | 300 |
| gggaccaagc | tggagatcag | ccgaactgtg | gctgcaccat | ctgtcttcat | cttcccg | 357 |

<210> SEQ ID NO 4
<211> LENGTH: 119
<212> TYPE: PRT
<213> ORGANISM: Homo sapiens

```
<400> SEQUENCE: 4

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Lys Pro Gly Gln Ala Pro Arg Leu Leu
        35                  40                  45

Ile Tyr Gly Ala Ser Arg Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Arg Tyr Gly Ser Ser His
                85                  90                  95

Thr Phe Gly Gln Gly Thr Lys Leu Glu Ile Ser Arg Thr Val Ala Ala
            100                 105                 110

Pro Ser Val Phe Ile Phe Pro
        115

<210> SEQ ID NO 5
<211> LENGTH: 5
<212> TYPE: PRT
<213> ORGANISM: Homo sapiens

<400> SEQUENCE: 5

Thr Tyr Trp Ile Gly
1               5

<210> SEQ ID NO 6
<211> LENGTH: 16
<212> TYPE: PRT
<213> ORGANISM: Homo sapiens

<400> SEQUENCE: 6

Ile Ile Tyr Pro Gly Asp Ser Asp Thr Arg Tyr Ser Pro Pro Phe Gln
1               5                   10                  15

<210> SEQ ID NO 7
<211> LENGTH: 8
<212> TYPE: PRT
<213> ORGANISM: Homo sapiens

<400> SEQUENCE: 7

Gly Asn Trp Asn Cys Phe Asp Tyr
1               5

<210> SEQ ID NO 8
<211> LENGTH: 12
<212> TYPE: PRT
<213> ORGANISM: Homo sapiens

<400> SEQUENCE: 8

Arg Ala Ser Gln Ser Val Ser Ser Ser Tyr Leu Ala
1               5                   10

<210> SEQ ID NO 9
<211> LENGTH: 7
<212> TYPE: PRT
<213> ORGANISM: Homo sapiens

<400> SEQUENCE: 9

Gly Ala Ser Arg Arg Ala Thr
```

```
1               5

<210> SEQ ID NO 10
<211> LENGTH: 8
<212> TYPE: PRT
<213> ORGANISM: Homo sapiens

<400> SEQUENCE: 10

Gln Arg Tyr Gly Ser Ser His Thr
1               5
```